(12) United States Patent
Zhou et al.

(10) Patent No.: US 8,993,303 B2
(45) Date of Patent: Mar. 31, 2015

(54) GENETICALLY ENGINEERED CYANOBACTERIA

(75) Inventors: Ruanbao Zhou, Brookings, SD (US); William Gibbons, Brookings, SD (US)

(73) Assignee: South Dakota State University, Brookings, SD (US)

( * ) Notice: Subject to any disclaimer, the term of this patent is extended or adjusted under 35 U.S.C. 154(b) by 158 days.

(21) Appl. No.: 13/405,208

(22) Filed: Feb. 24, 2012

(65) Prior Publication Data

US 2012/0276637 A1 Nov. 1, 2012

Related U.S. Application Data

(60) Provisional application No. 61/446,366, filed on Feb. 24, 2011, provisional application No. 61/522,685, filed on Aug. 11, 2011.

(51) Int. Cl.
*C12N 1/21* (2006.01)
*C12N 15/00* (2006.01)

(52) U.S. Cl.
USPC .............. 435/252.3; 435/243; 435/252.1; 435/320.1

(58) Field of Classification Search
None
See application file for complete search history.

(56) References Cited

U.S. PATENT DOCUMENTS

| | | | |
|---|---|---|---|
| 6,699,696 B2 | 3/2004 | Woods et al. | |
| 7,531,333 B2 * | 5/2009 | Miyake et al. | 435/166 |
| 7,659,097 B2 * | 2/2010 | Renninger et al. | 435/157 |
| 7,794,969 B1 | 9/2010 | Reppas et al. | |
| 2009/0203070 A1 * | 8/2009 | Devroe et al. | 435/69.1 |
| 2010/0003739 A1 * | 1/2010 | Duhring et al. | 435/252.3 |
| 2011/0039323 A1 * | 2/2011 | Singsaas et al. | 435/167 |

FOREIGN PATENT DOCUMENTS

WO 2007084477 A1 7/2007

OTHER PUBLICATIONS

A Tomar et al. The Effect of Acetate Pathway Mutations on the Production of Pyruvate in *Escherichia coli*, Applied Microbiology and Biotechnology, 2003, vol. 62, pp. 76.
Mai Li et al. Effect of lpdA Gene Knockout on the Metabolism in *Escherichia coli* Based on Enzyme Activities, Intracellular Metabolite Concentrations and Metabolic Flux Analysis by 13C-labeling Experiments, Journal of Biotechnology, 2006, vol. 122, pp. 254.
Xiaojie Pan et al. Morphological Characteristics and Phylogenetic Relationship of *Anabaena* Species from Lakes Dianchi and Erhai, China, Hydrobiologia, 2008, vol. 614, pp. 353.
Ruanbao Zhou and C. Peter Wolk, A Two-component System Mediates Developmental Regulation of Biosynthesis of a Heterocyst Polysaccharide, Journal of Biological Chemistry, 2003, vol. 278 (22), pp. 19939.
Yoshiko Miyagawa et al. Overexpression of a Cyanobacterial Fructose-1,6-/Sedoheptulose-1,7-Bisphosphatase in Tobacco Enhances Photosynthesis and Growth, Nature Biotechnology, 2001, vol. 19, pp. 965.
T. Iwaki et al. Expression of Foreign Type I Ribulose-1,5-Bisphosphate Carboxylase/Oxygenase (EC 4.1.1.39) Stimulates Photosynthesis in Cyanobacterium *Synechococcus* PCC7942 Cells, Photosynthesis Research, 2006, vol. 88, pp. 287.
Masahiro Tamoi et al. Contribution of Fructose-1,6-Bisphosphate and Sedoheptulose-1,7-Bisphosphatase to the Photosynthetic Rate and Carbon Flow in the Calvin Cycle in Transgenic Plants, Plant Cell Physiology, 2006, vol. 47 (3), pp. 380.

* cited by examiner

*Primary Examiner* — Oluwatosin Ogunbiyi
(74) *Attorney, Agent, or Firm* — MDIP LLC

(57) ABSTRACT

The disclosed embodiments provide cyanobacteria spp. that have been genetically engineered to have increased production of carbon-based products of interest. These genetically engineered hosts efficiently convert carbon dioxide and light into carbon-based products of interest such as long chained hydrocarbons. Several constructs containing polynucleotides encoding enzymes active in the metabolic pathways of cyanobacteria are disclosed. In many instances, the cyanobacteria strains have been further genetically modified to optimize production of the carbon-based products of interest. The optimization includes both up-regulation and down-regulation of particular genes.

10 Claims, 13 Drawing Sheets

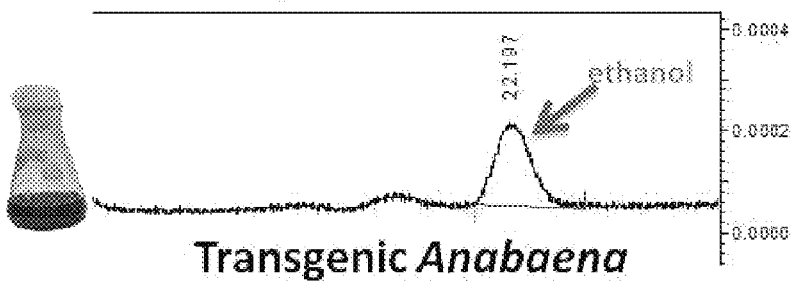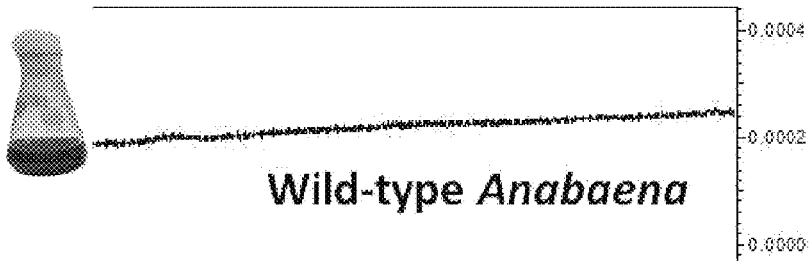
FIG. 3

FIG. 7. Mass spectra for linalool standard

FIG. 8. Mass spectra for linalool produced by engineered *Anabaena* (see FIG. 6B)

FIG. 9. Hydrocarbons produced by *Anabaena cylindrica* 29414

FIG. 10. Engineering *Anabaena* to synthesize urea using solar energy

FIG.11. Sucrose produced by *Anabaena* sp PCC7120

A LinS gene is integrated to *Anabena* chromosome at loci A and B

Homologous genes from MEP pathway found in five cyanobacterial strains*

| | Arabidopsis thaliana | Anabaena sp. PCC 7120 | Anabaena variabilis ATCC 29413 | Thermosyne-chococcus elongatus BP-1 | Synechocystis sp. PCC 6803 | Nostoc punctiforme ATCC 29133 |
|---|---|---|---|---|---|---|
| DXS | | alr0599 | Ava_4532 | tll0623 | sll1945 | Npun_F5466 |
| | AT3G21500 (DXS1) | 1E-137 | 1E-138 | 1E-143 | 1E-139 | 1E-135 |
| | AT4G15560 (DXS2) | 1E-148 | 1E-149 | 1E-155 | 1E-149 | 1E-144 |
| | AT5G11380 (DXS3) | 1E-110 | 1E-110 | 1E-109 | 1E-103 | 1E-105 |
| DXR | AT5G62790 | alr4351 | Ava_1300 | tlr1040 | sll0019 | Npun_R5970 |
| | | 1E-151 | 1E-152 | 1E-147 | 1E-145 | 1E-151 |
| MCT | AT2G02500 | all5167 | Ava_2414 | tll0605 | sll0951 | Npun_F5020 |
| | | 2E-28 | 8E-28 | 5E-32 | 8E-28 | 3E-26 |
| CMK | AT2G26930 | alr3230 | Ava_4887 | tll0500 | slr0711 | Npun_R4911 |
| | | 1E-22 | 2E-22 | 6E-22 | 5E-20 | 2E-21 |
| MDS | AT1G63970 | alr3883 | Ava_1811 | tlr2035 | slr1542 | Npun_F5826 |
| | | 2E-38 | 2E-38 | 2E-38 | 6E-38 | 4E-38 |
| HDS | AT5G60600 | all2501 | Ava_0433 | tll0996 | slr2136 | Npun_F5054 |
| | | 2E-73 | 4E-73 | 5E-70 | 1E-72 | 1E-72 |
| HDR | AT4G34350 | all0985 | Ava_2948 | tlr1041 | slr0348 | Npun_R3286 |
| | | 1E-148 | 1E-148 | 1E-145 | 1E-144 | 1E-142 |
| IDI | AT5G16440 (IDI1) | None | None | None | None | None |
| | AT3G02780 (IDI2) | None | None | None | None | None |
| GPPS | | alr0096 | Ava_1469 | tlr1757 | slr0611 | Npun_R1834 |
| | AT1G78510 (GPPS1) | 1E-95 | 4E-97 | 2E-98 | 4E-99 | 1E-95 |
| | AT2G34630 (GPPS2) | 2E-61 | 2E-62 | 2E-58 | 2E-61 | 2E-62 |
| FPPS | | alr0096 | Ava_1469 | tll0020 | sll0739 | Npun_R1834 |
| | AT5G47770 (FPPS1) | 6E-04 | 2E-03 | 5E-06 | 5E-04 | 3E-04 |
| | AT4G17190 (FPPS2) | 4E-04 | 5E-05 | 5E-05 | 6E-03 | 1E-04 |
| GGPPS | | alr0213 | Ava_2704 | tll0020 | sll0739 | Npun_F3770 |
| | AT4G36810 (GGPPS1) | 6E-89 | 2E-88 | 1E-99 | 7E-88 | 1E-88 |
| | AT2G23800 (GGPPS2) | 4E-76 | 3E-77 | 2E-78 | 2E-75 | 2E-80 |
| | AT3G14510 (GGPPS3) | 4E-79 | 6E-79 | 1E-84 | 3E-84 | 3E-81 |
| | AT2G18640 (GGPPS4) | 8E-76 | 1E-76 | 1E-79 | 7E-77 | 1E-79 |
| | AT1G49530 (GGPPS5) | 6E-67 | 1E-66 | 3E-65 | 7E-77 | 2E-68 |
| | AT3G14530 | 2E-79 | 3E-79 | 8E-85 | 1E-85 | 5E-82 |
| | AT3G32040 | 1E-77 | 8E-78 | 4E-81 | 4E-81 | 3E-79 |
| SQS | | alr1809 | Ava_4030 | tll1096 | sll0513 | Npun_R2917 |
| | AT4G34640 (SQS1) | 3E-08 | 2E-07 | 3E-16 | 2E-09 | 2E-06 |
| | AT4G34650 (SQS2) | 4E-05 | 8E-05 | 1E-13 | 1E-07 | 1E-04 |
| LinS | AT1G61680 (TPS14) | None | None | None | None | None |

* Arabidopsis genes were used for Blast search, single gene found in each genome and its E-value included

GENETICALLY ENGINEERED CYANOBACTERIA

CROSS-REFERENCE TO RELATED APPLICATIONS

This application claims priority to U.S. Provisional Patent Application Ser. No. 61/446,366, filed Feb. 24, 2011, and U.S. Provisional Patent Application Ser. No. 61/522,685, filed Aug. 11, 2011, the entire contents of each of which are incorporated herein by reference.

STATEMENT REGARDING FEDERALLY SPONSORED RESEARCH OR DEVELOPMENT

This invention was made with U.S. Government Support from the following agencies: USDA (Grant #SA1100114), NSF (Grant #CBET1133951), and NASA (Grant #NNX11AM03A). The U.S. Government has certain rights in this invention.

TECHNICAL FIELD

The present disclosure relates to compositions and methods for the production of carbon-based products of interest such as biofuels and high value chemicals by genetically engineered cyanobacteria hosts. The genetically engineered cyanobacteria hosts are optimized for use in production of carbon-based products of interest by strengthening endogenous metabolic pathways of cyanobacteria. In certain instances, competing metabolic pathways are down-regulated. Methods of making and using the genetically engineered cyanobacteria hosts are also described.

BACKGROUND

Many existing photoautotrophic organisms are poorly suited for industrial bioprocessing and have therefore not demonstrated commercial viability. Although aquatic photoautotrophs, such as cyanobacteria, may exhibit rapid growth rates and efficient photosynthetic pathways, giving them tremendous potential for sustainable production of carbon-based products of interest from only $CO_2$, $N_2$, and sunlight, they have not yet been optimized for production. Such organisms typically require large amounts of water usage as well as time and energy to harvest biomass. Therefore, a need exists to modify existing photoautotroph hosts such that these drawbacks can be overcome.

SUMMARY

The present disclosure includes compositions and methods for the production of carbon based products of interest using genetically modified cyanobacteria such as Anabaena spp. In certain embodiments, the Anabaena spp. are Anabaena PCC7120, Anabaena cylindrica 29414, or Anabaena variabilis ATCC29413. In one aspect of the disclosure, the Anabaena spp. is the ethanol producing Anabaena sp. PCC7120 (pZR672) strain deposited under ATCC accession number PTA-12833 or the linalool producing Anabaena sp. PCC7120 (pZR808) strain deposited under ATCC accession number PTA-12832. Generally the Anabaena spp. is genetically engineered by expression of at least one recombinant polynucleotide expression construct comprising an enzyme capable of increasing production of a carbon based product of interest.

The carbon based product of interest may be ethanol or linolool. In many embodiments, the MEP pathway of the Anabaena spp. is up-regulated by modifying at least one gene responsible for control of the MEP pathway in the Anabaena spp. Photosynthesis of the Anabaena spp. may also be increased through genetic modification. For example, a polynucleotide expression construct comprising a nucleotide sequence encoding RuBisCo and/or RuBisCo activase is contemplated.

In certain embodiments, the Anabaena spp. is further genetically modified to produce enzymes capable of increasing specific production of ethanol or linolool. For example, in embodiments that specifically produce ethanol, the Anabaena spp. may be genetically engineered to produce decarboxylase (PDC) or alcohol dehydrogenase (ADH). In embodiments specifically producing linolool, the Anabaena spp. may be genetically engineered to produce linalool synthase.

A disclosed method includes producing a genetically engineered Anabaena spp. capable of making a carbon based product of interest by introducing a recombinant enzyme into the Anabaena spp, wherein the recombinant enzyme can participate in the Anabaena spp's natural metabolic pathway, and modifying at least one competing metabolic pathway to increase production of the carbon based product of interest. In one disclosed aspect, the Anabaena spp. is the ethanol producing Anabaena sp. PCC7120 (pZR672) strain deposited under ATCC accession number PTA-12833 or the linalool producing Anabaena sp. PCC7120 (pZR808) strain deposited under ATCC accession number PTA-12832. The natural metabolic pathway may be the MEP pathway or the photosynthetic pathway and the carbon based product of interest may be ethanol or linalool.

BRIEF DESCRIPTION OF THE DRAWINGS

FIG. 3 is ethanol productivity in genetically engineered Anabaena as measured by HPLC.

FIG. 13 shows a table of the MEP pathway genes in cyanobacteria.

DETAILED DESCRIPTION

Figure 1:
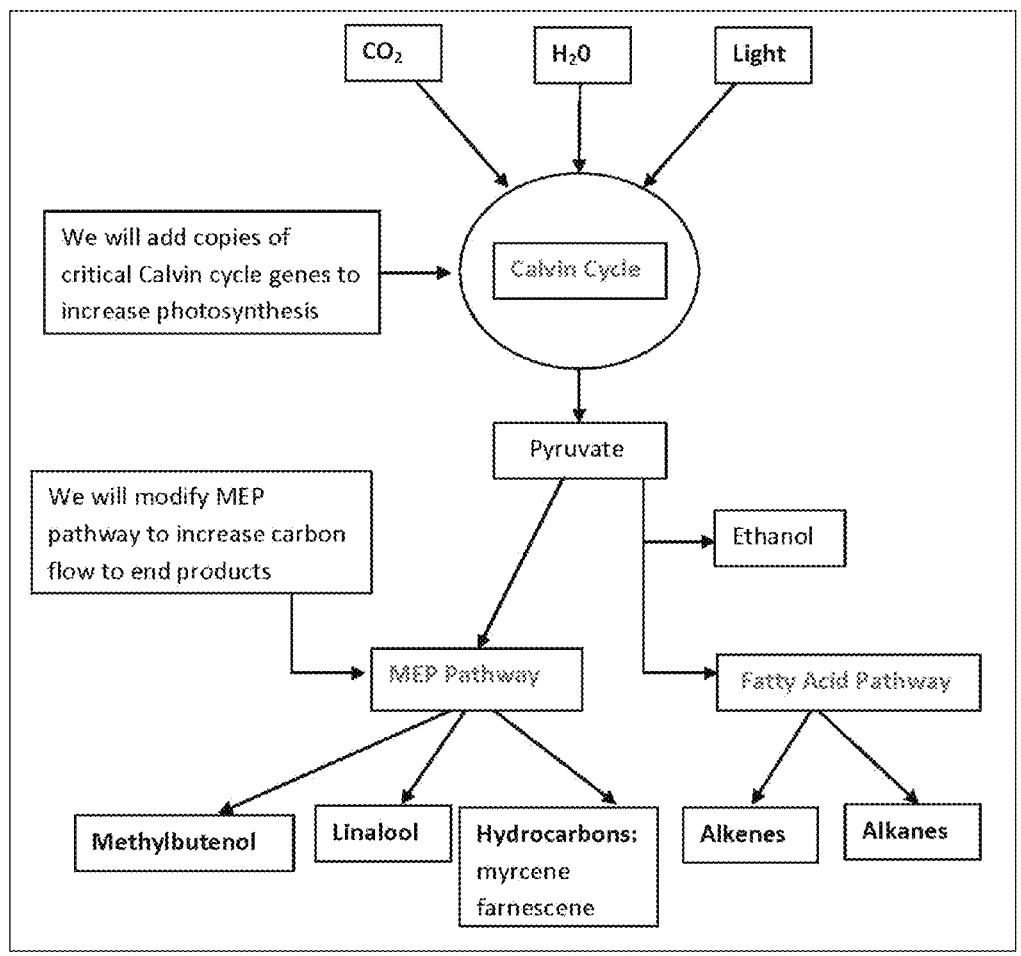
FIG. 1 demonstrates the presumptive cyanobacterial carbon metabolic pathways for production of biofuels and high value chemicals.

For describing invention herein, the exemplary embodiments in detail, it is to be understood that the embodiments are not limited to particular compositions or methods, as the compositions and methods can, of course, vary. It is also to be understood that the terminology used herein is for the purpose of describing particular embodiments only, and is not intended to be limiting. Unless defined otherwise, all technical and scientific terms used herein have the same meaning as commonly understood by one of ordinary skill in the art to which an embodiment pertains. Many methods and compositions similar, modified, or equivalent to those described herein can be used in the practice of the current embodiments without undue experimentation.

As used in this specification and the appended claims, the singular forms "a," "an" and "the" can include plural referents unless the content clearly indicates otherwise. Thus, for example, reference to "a cytokine" can include a combination of two or more cytokines. The term "or" is generally employed to include "and/or," unless the content clearly dictates otherwise.

As used herein, "about," "approximately," "substantially," and "significantly" will be understood by person of ordinary skill in the art and will vary in some extent depending on the context in which they are used. If there are uses of the term which are not clear to persons of ordinary skill in the art given the context in which it is used, "about" and "approximately" will mean plus or minus ≤10% of particular term and "substantially" and "significantly" will mean plus or minus >10% of the particular term.

The term "polynucleotide" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native internucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation. An "isolated" polynucleotide is one which is substantially separated from other cellular components that naturally accompany the native polynucleotide in its natural host cell, e.g., ribosomes, polymerases and genomic sequences with which it is naturally associated.

Polynucleotides may include both sense and antisense strands of RNA, cDNA, genomic DNA, and synthetic forms and mixed polymers of the above. They may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) Also included are synthetic molecules that mimic polynucleotides in their ability to bind to a designated. In certain embodiments, the polynucleotides are modified such that they contain preferential codon sequence for the host.

The term "percent sequence identity" or "identical" in the context of polynucleotide sequences refers to the residues in the two sequences which are the same when aligned for maximum correspondence. The term "substantial homology" or "substantial similarity," when referring to a polynucleotide, indicates that, when optimally aligned with appropriate nucleotide insertions or deletions with another polynucleotide (or its complementary strand), there is nucleotide sequence identity in at least about 76%, 80%, 85%, at least about 90%, and at least about 95%, 96%, 97%, 98% or 99% of the nucleotide bases, as measured by any well-known algorithm of sequence identity.

A heterologous sequence is a sequence that is in a different position or in a different amount than what is found in nature, whether or not the heterologous sequence is itself endogenous (originating from the same host cell or progeny thereof) or exogenous (originating from a different host cell or progeny thereof).

A recombinant molecule is a molecule, e.g., a gene or protein, that (1) has been removed from its naturally occurring environment, (2) is not associated with all or a portion of a polynucleotide in which the gene is found in nature, (3) is operably linked to a polynucleotide which it is not linked to in nature, or (4) does not occur in nature. In many embodiments, the recombinant molecule is an enzyme. The term "recombinant" can be used in reference to cloned DNA isolates, chemically synthesized polynucleotide analogs, or polynucleotide analogs that are biologically synthesized by heterologous systems, as well as proteins and/or mRNAs encoded by such nucleic acids. A coding sequence is considered "recombinant" if it contains an insertion, deletion or a point mutation introduced artificially, e.g., by human intervention.

Molecules are "operably linked" if there is a functional relationship between two parts in which the activity of one part (e.g., the ability to regulate transcription) results in an action on the other part (e.g., transcription of the sequence). Thus, a polynucleotide is "operably linked to a promoter" when there is a functional linkage between a polynucleotide expression control sequence (such as a promoter or other transcription regulation sequences) and a second polynucleotide sequence (e.g., a heterologous polynucleotide), where the expression control sequence directs transcription of the polynucleotide.

An "expression vector" or "construct" refers to a series of polynucleotide elements that are capable of transporting the polynucleotide elements into the host and permitting transcription of a gene in a host cell. Most embodiments require that the host have activity of the gene product as a consequence of being genetically engineered with an expression vector. For example, if the expression vector includes polynucleotide elements encoding a gene for an enzyme, the enzyme should have enzymatic activity after the host is genetically engineered. Typically, the expression vector includes a promoter and a heterologous polynucleotide sequence that is transcribed. Expression vectors or constructs may also include, e.g., transcription termination signals, polyadenylation signals, and enhancer elements. Constructs may also include polynucleotides that make them temperature sensitive, antibiotic resistant, or chemically inducible. Expression vectors can replicate autonomously, or they can replicate by being inserted into the genome of the host cell. In exemplary embodiment, the construct encoding the desired enzyme is present on a "plasmid," which generally refers to a circular double stranded DNA loop into which additional DNA segments may be ligated, but also includes linear double-stranded molecules such as those resulting from amplification by the polymerase chain reaction (PCR) or from treatment of a circular plasmid with a restriction enzyme.

The term "recombinant host cell" or "engineered host cell" (or simply "host cell" or "host") refers to a cell into which a recombinant polynucleotide has been introduced. Recombinant polynucleotides can be used to transform a variety of hosts to produce a carbon-based product of interest. The host must be "competent to express," such that it provides a sufficient cellular environment for expression of endogenous and/or exogenous polynucleotides. A recombinant host cell may be an isolated cell or cell line grown in culture or may be a cell which resides in a living tissue or organism. Photoautotrophic organism hosts include organisms such as eukaryotic plants and algae, as well as prokaryotic cyanobacteria, green-sulfur bacteria, green non-sulfur bacteria, purple sulfur bacteria, and purple non-sulfur bacteria.

In embodiments, the engineered cell of the invention is an algae and/or cyanobacterial organism selected from the group consisting of Acanthoceras, Acanthococcus, Acaryochloris, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogloeopsis, Chlorogonium, Chlorolobion, Chloromonas, Chlorophysema, Chlorophyta, Chlorosaccus, Chlorosarcina, Choricystis, Chromophyton, Chromulina, Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleum, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Micro cystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum,

*Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spennatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloea, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thermosynechococcus, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium*. In yet other related embodiments, the engineered cell provided by the invention is derived from a *Chloroflexus, Chloronema, Oscillochloris, Heliothrix, Herpetosiphon, Roseiflexus,* and *Thermomicrobium* cell; a green sulfur bacteria selected from: *Chlorobium, Clathrochloris,* and *Prosthecochloris*; a purple sulfur bacteria is selected from: *Allochromatium, Chromatium, Halochromatium, Isochromatium, Marichromatium, Rhodovulum, Thermochromatium, Thiocapsa, Thiorhodococcus,* and *Thiocystis*; a purple non-sulfur bacteria is selected from: *Phaeospirillum, Rhodobaca, Rhodobacter, Rhodomicrobium, Rhodopila, Rhodopseudomonas, Rhodothalassium, Rhodospirillum, Rodovibrio,* and *Roseospira*; an aerobic chemolithotrophic bacteria selected from: nitrifying bacteria. *Nitrobacteraceae* sp., *Nitrobacter* sp., *Nitrospina* sp., *Nitrococcus* sp., *Nitrospira* sp., *Nitrosomonas* sp., *Nitrosococcus* sp., *Nitrosospira* sp., *Nitrosolobus* sp., *Nitrosovibrio* sp.; colorless sulfur bacteria such as, *Thiovulum* sp., *Thiobacillus* sp., *Thiomicrospira* sp., *Thiosphaera* sp., *Thermothrix* sp.; obligatory chemolithotrophic hydrogen bacteria, *Hydrogenobacter* sp., iron and manganese-oxidizing and/or depositing bacteria, *Siderococcus* sp., and magnetotactic bacteria, *Aquaspirillum* sp; an archaeobacteria selected from: methanogenic archaeobacteria, *Methanobacterium* sp., *Methanobrevibacter* sp., *Methanothermus* sp., *Methanococcus* sp., *Methanomicrobium* sp., *Methanospirillum* sp., *Methanogenium* sp., *Methanosarcina* sp., *Methanolobus* sp., *Methanothrix* sp., *Methanococcoides* sp., *Methanoplanus* sp.; extremely thermophilic sulfur-Metabolizers such as *Thermoproteus* sp., *Pyrodictium* sp., *Sulfolobus* sp., *Acidianus* sp., *Bacillus subtilis, Saccharomyces cerevisiae, Streptomyces* sp., *Ralstonia* sp., *Rhodococcus* sp., *Corynebacteria* sp., *Brevibacteria* sp., *Mycobacteria* sp., and oleaginous yeast; and extremophile selected from *Pyrolobus fumarii; Synechococcus lividis,* mesophiles, psychrophiles, *Psychrobacter,* insects, *Deinococcus radiodurans*, piezophiles, barophiles, hypergravity tolerant organisms, hypogravity tolerant organisms, vacuum tolerant organisms, tardigrades, insects, microbes seeds, dessicant tolerant anhydrobiotic organisms, xerophiles, *Artemia salina,* nematodes, microbes, fungi, lichens, salt tolerant organisms halophiles, halobacteriacea, *Dunaliella salina*, pH tolerant organisms, alkaliphiles, *Natronobacterium, Bacillus firmus* OF4, *Spirulina* spp., acidophiles, *Cyanidium caldarium, Ferroplasma* sp., anaerobes, which cannot tolerate $O_2$, *Methanococcus jannaschii,* microaerophils, which tolerate some $O_2$, *Clostridium,* aerobes, which require $O_2$, gas tolerant organisms, which tolerate pure $CO_2$, *Cyanidium caldarium,* metal tolerant organisms, metalotolerants, *Ferroplasma acidarmanus Ralstonia* sp CH34.

In certain embodiments, the host is *Nostoc punctiforme* ATCC29133. In many embodiments, the host is an *Anabaena* spp of cyanobacterium. *Anabaena* provides several advantages above the cyanobacteria currently being genetically modified to produce carbon based products of interest. For example, *Anabaena* is capable of fixing its own $N_2$ for growth using heterocysts using only solar energy and water, allowing for less investment for growth. In one embodiment, the host is *Anabaena* PCC7120 (*Anabaena* 7120). In another embodiment, the host is *Anabaena cylindrica* 29414. In yet another embodiment, the host is *Anabaena variabilis* ATCC29413.

"Carbon-based products of interest" include alcohols such as ethanol, propanol, methylbutenol, linalool, geraniol, isopropanol, butanol, butanetriol, menthol, fatty alcohols, fatty acid esters, wax esters; hydrocarbons (alkanes/alkenes) such as propane, hexane, octane/octane, squalane, myrcene, decene, pinene, farnesene, limonene, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, .epsilon.-caprolactone, isoprene, caprolactam, rubber; commodity chemicals such as lactate, Docosahexaenoic acid (DHA), 3-hydroxypropionate, amino acids such as lysine, serine, aspartate, and aspartic acid, sorbitol, ascorbate, ascorbic acid, isopentenol, lanosterol, omega-3 DHA, itaconate, 1,3-butadiene, ethylene, propylene, succinate, citrate, citric acid, sucrose, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals including carotenoids such as lycopene, astaxanthin, β-carotene, and canthaxanthin, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, i.e. any fuel with one or more hydrocarbons, one or more alcohols, one or more fatty esters or a mixture thereof that derives from a biological source industrial and specialty chemicals, as intermediates used to make additional products, such as nutritional supplements, neutraceuticals, polymers, paraffin replacements, personal care products and pharmaceuticals.

In various embodiments, polynucleotides encoding enzymes are introduced into the host cell such that expression of the enzyme by the host under certain conditions results in increased production of a carbon-based product of interest. In certain cases, introduction takes place through transformation of the host. "Increased production" or "up-regulation" of a carbon-based product of interest includes both augmentation of native production of the carbon-based product of interest as well as production of a carbon-based product of interest in an organism lacking native production. For example, in some instances production will be increased from a measurable initial value whereas in other instances the initial value is zero.

A recombinant expression construct for transformation of a host cell and subsequent integration of the gene(s) of interest is prepared by first isolating the constituent polynucleotide sequences. In some embodiments, the gene(s) of interest are homologously integrated into the host cell genome. In other embodiments, the genes are non-homologously integrated into the host cell genome. Generally, constructs containing polynucleotides are introduced into the host cell using a standard protocol, such as the one set out in Golden S S et al. (1987) "Genetic engineering of the Cyanobacteria chromosome" *Methods Enzymol* 153: 215-231 and in S. S. Golden and L. A. Sherman, *J. Bacteriol.* 158:36 (1984), incorporated herein by reference. The particular procedure used to introduce the genetic material into the host cell for expression is not particularly critical. Any of the well-known procedures for introducing heterologous polynucleotide sequences into host cells can be used. In certain embodiments, only a single copy of the heterologous polynucleotide is introduced. In other embodiments, more than a single copy, such as two copies, three copies or more than three copies of the heterologous polynucleotide is introduced. As is understood by the skilled artisan, multiple copies of heterologous polynucleotides may be on a single construct or on more than one construct.

In exemplary embodiments, the disclosed polynucleotides are operably connected to a promoter in the construct. As is understood in the art, a promoter is segment of DNA which acts as a controlling element in the expression of that gene. In one embodiment, the promoter is a native *Anabaena* promoter. For example, the promoter may be an *Anabaena* Pnir promoter such as the one described in Desplancq, D2005, Combining inducible protein overexpression with NMR-grade triple isotope labeling in the cyanobacterium *Anabaena* sp. PCC 7120. *Biotechniques.* 39:405-11 (SEQ ID NO. 1) or one having sequence identity of about 76%, 80%, 85%, at least about 90%, and at least about 95%, 96%, 97%, 98% or 99% to SEQ ID NO. 1. The promoter may also be an *Anabaena* psbA promoter (SEQ ID NO. 2), Prbc$_L$ promoter (SEQ ID NO. 3) and/or *E. coli* P$_{tac}$ promoter (SEQ ID NO. 4) (Elhai, J. 1993. Strong and regulated promoters in the cyanobacterium *Anabaena* PCC 7120. *FEMS Microbiol Lett.* 114(2): 179-84) or one having sequence identity of about 76%, 80%, 85%, at least about 90%, and at least about 95%, 96%, 97%, 98% or 99% to SEQ ID NO. 2, SEQ ID NO. 3, or SEQ ID NO. 4. In some embodiments, the promoter is a combined dual promoter, i.e. a promoter containing more than one of the above.

In some embodiments, the gene of interest is transiently introduced into the host cell through use of a plasmid or shuttle vector. In other embodiments, the gene of interest is permanently introduced into the chromosome of the host cell. Chromosomal integration techniques are known to the skilled artisan and have been described in Zhou and Wolk, 2002, Identification of an Akinete Marker Gene in *Anabaena variabilis*, *J. Bacteriol.*, 184(9):2529-2532. Briefly, the gene of interest is fused to a promoter and then subcloned into an integration vector. This construct is introduced into the host cell for double homologous recombination at specific loci on the host cell chromosome. In many embodiments, homologous recombination takes place at two loci of the host cell chromosome. The recombinant cells can be selected by monitoring loss of a conditional lethal gene, such as sacB. Further diagnostic verification by the polymerase chain reaction can be performed. In many embodiments, the gene of interest will be inserted into the chromosome at the site of a gene that is desired to be deleted or inactivated.

After the host is genetically modified, the host is generally incubated under conditions suitable for production of the carbon-based product of interest. Culture conditions for various hosts are well documented in the literature. Typically, when the host is *Anabaena*, the host cell will be grown in a photoautotrophic liquid culture in BG-11 media, with an 1 L/min air sparge rate and a pH set point of 7.5, controlled via sparging with $CO_2$, and the temperature maintained at 30° C.

In many embodiments, strain engineering techniques such as directed evolution and acclimation will be used to improve the performance of various host cells. Strain engineering is known in the art (Hughes, S. R., K. M. Bischoff, W. R. Gibbons, S. S. Bang, R. Pinkelman, P. J. Slininger, N. Qureshi, S. Liu, B. C. Saha, J. S. Jackson, M. C. Cotta, J. O. Rich, and J. Javers. 2011. Random UV-C Mutagenesis of *Scheffersomyces* (formerly *Pichia*) *stipitis* NRRL Y-7124 to Improve Anaerobic Growth on Lignocellulosic Sugars. *J. Ind. Microbiol. Biotechnol.* DOI 10.1007/x 10295-011-1012-x; Bock, S. A., Fox, S. L. and Gibbons. W. R. 1997. Development of a low cost, industrially suitable medium for production of acetic acid from glucose by *Clostridium thermoaceticum*. *Biotechnol. Applied Bioch*. 25:117-125; Gibbons, W. R., N. Pulseher, and E. Ringquist. 1992. Sodium meta bisulfite and pH tolerance of *Pleurotus sajor caju* under submerged cultivation. *Appl. Biochem. Biotechnol.* 37:177-189.

As host cells generally possess complex regulatory systems for traits such as product tolerance, productivity, and yield, directed evolution and screening is often used to create global genome-wide alterations needed to develop strains with desired industrial characteristics. Certain embodiments will use directed evolution under elevated linalool concentrations, as well as fluctuating temperature, pH, and $CO_2/O_2$ levels to generate stable, heritable genetic improvements in product tolerance, productivity, yield, and robustness to process conditions.

A. Ethanol

In one embodiment, the host cell is genetically engineered to increase production of ethanol through transformation with an expression vector containing polynucleotides encoding ethanol producing enzymes. As used herein, an ethanol producing enzyme is an enzyme active in the end production of ethanol from a precursor molecule in a metabolic pathway. The polynucleotide encodes pyruvate decarboxylase (SEQ ID NO. 5) and/or alcohol dehydrogenase (SEQ ID NO. 6) in exemplary embodiments. Embodiments also include enzymes having sequence identity of about 76%, 80%, 85%, at least about 90%, and at least about 95%, 96%, 97%, 98% or 99% to SEQ ID NO. 5 and SEQ ID NO. 6. The host is genetically engineered with polynucleotides encoding one or both enzymes. In many embodiments, host cells are engineered to express both enzymes. Known sources of polynucleotides encoding pyruvate decarboxylase and alcohol dehydrogenase exist. For example, the nucleic acid encoding the enzymes may be from organisms such as *Zymomonas mobilis, Zymobacter paimae*, or *Saccharomyces cerevisciae* (Ingram L O, Conway T, Clark D P, Sewell G W, Preston J F. 1987. Genetic engineering of ethanol production in *Escherichia coli*. Appl Environ Microbiol. 53(10):2420-5). Any pyruvate decarboxylase (pdc) gene capable of expression in the host may be used in with the disclosed embodiments. In some embodiments, the pdc gene is the *Zymomonas mobilis* pdc gene. In these embodiments, the pdc gene is often obtained from the *Zymomonas mobilis* plasmid pLOI295. In other embodiments, the pdc gene is from *Zymobacter paimae*. The NCBI accession number for the complete pdc protein sequence from *Zymobacter paimae* is AF474145. Similarly, any alcohol dehydrogenase (adh) gene capable expression in the host may be used with the disclosed embodiments. In some embodiments, the adh gene is the *Zymomonas mobilis* adhII gene. In these embodiments, the adh gene is often obtained from the *Zymomonas mobilis* plasmid pLOI295.

Polynucleotides encoding genes such as omrA, lmrA, and lmrCD, which increase the ability of the host to handle commercially relevant amounts of ethanol, may be included on the same or a different vector as the polynucleotides encoding the pdc and adh genes. Bourdineaud J P, Nehmé B, Tesse S, Lonvaud-Funel A. 2004. A bacterial gene homologous to ABC transporters protect Oenococcus oeni from ethanol and other stress factors in wine. *Int. J. Food Microbiol.* 92(1):1-14. For example, in some embodiments, the expression vector comprising the pdc/adh genes further comprises the omrA gene. In other embodiments, the expression vector comprising the pdc/adh genes further comprises the lmrA gene. In yet other embodiments, the expression vector comprising the pdc/adh genes further comprises the lmrCD gene. And in still further embodiments, the expression vector comprising the pdc/adh genes further comprises polynucleotides encoding the omrA, lmrA, and lmrCD genes.

In host cells producing increased ethanol, the synthesis of pyruvate is additionally up-regulated in certain embodiments. In these embodiments, phosphoglycerate mutase, enolase, and/or pyruvate kinase, are over-expressed. A construct containing genes of one or more of the above enzymes is designed using genes from *Z. mobilis* and *S. cerevisiae*. The construct is then used to genetically engineer a host.

Ethanol producing *Anabaena* sp. PCC7120 (pZR672) strain was deposited at the American Type Culture Collection on Feb. 27, 2012, and given accession number PTA-12833. PTA-12833 was deposited with the American Type Culture Collection ATCC at 10801 University Blvd. Manassas Va. 20110-2209 USA. The deposit was made under the provisions of the Budapest Treaty on the International Recognition of Deposited microorganisms for the Purposes of Patent Procedure and Regulations thereunder Budapest Treaty). Maintenance of a viable culture is assured for thirty years from the date of deposit. The organism will be made available by the ATCC under the terms of the Budapest Treaty, and subject to an agreement between the Applicants and the ATCC which assures unrestricted availability of the deposited cells to the public upon the granting of patent from the instant application.

B. Sucrose

In yet another embodiment, the host cell is engineered to increase the production and excretion of sucrose through transformation with an expression vector containing polynucleotides encoding sucrose producing enzymes. As used herein, a sucrose producing enzyme is an enzyme active in the end production of sucrose from a precursor molecule in a photosynthetic pathway. In these embodiments, a polynucleotide encoding sucrose-phosphate synthase (SPS) and/or sucrose-phosphate phosphatase (SPP) is introduced into the host cell and expressed such that the host cell increases its production of sucrose. Known sources of SPS and SPP exist and any SPS or SPP gene capable of expression may be used with the disclosed embodiments. For example, polynucleotide encoding SPS and SPP may be from organisms such as sugar beet and sugar cane such as those in SEQ ID NO. 7, SEQ ID NO. 8, SEQ ID NO. 9. In other embodiments, the polynucleotides have sequence identity of about 76%, 80%, 85%, at least about 90%, and at least about 95%, 96%, 97%, 98% or 99% to SEQ ID NO. 7, SEQ ID NO. 8, and SEQ ID NO. 9. In an alternative embodiment, the polynucleotide encoding SPS and is from cyanobacteria such as *Synchocystis, Anabaena*, or the like. Polynucleotides of SPS from cyanobacteria are shown in SEQ ID NO. 10 and SEQ ID NO. 11. In certain embodiments, SPS polynucleotides have sequence identity of about 76%, 80%, 85%, at least about 90%, and at least about 95%, 96%, 97%, 98% or 99% to SEQ ID NO. 10 and SEQ ID NO. 11.

In exemplary embodiments, the expression vector encoding SPS and/or SPP includes a promoter. For example, in some embodiments, the expression vector includes an *Anabaena* PpsbA promoter. In this embodiment the expression vector may be shuttle vector pRL489, such as the one described in Elhai J 1993 Strong and regulated promoters in the cyanobacterium *Anabaena* PCC7120. *FEMS Microbiol. Lett.* 114(2): 179-84.

In many embodiments where sucrose production has been increased, intracellular sucrose concentrations are reduced by over-expression of sucrose exporter genes. A sucrose exporter gene is a gene encoding a polypeptide involved in the transport of sucrose out of the cell. An example sucrose exporter gene includes the sucrose exporter gene from maize, i.e. ZmSUT1 (Slewinski et al., 2009. Sucrose transporter 1 functions in phloem loading in maize leaves. *J. Exp. Bot.* 60 (3):881-892). A sucrose exporter gene is demonstrated by SEQ ID NO. 12. In some embodiments, the sucrose exporter genes have sequence identity of about 76%, 80%, 85%, at least about 90%, and at least about 95%, 96%, 97%, 98% or 99% to SEQ ID NO. 12. The host in certain embodiments is genetically engineered with a sucrose exporter gene which is on the same construct as SPS and/or SPP. In other embodiments, the sucrose exporter genes may be from sugarcane and cloned into a separate expression vector or integrated into the chromosome of the host cells. Reinders A, Sivitz A B, Hsi A, Grof C P, Perroux J M, Ward J M. 2006. Sugarcane ShSUT1: analysis of sucrose transport activity and inhibition by sucralose. *Plant Cell Environ.* 29(10):1871-80 demonstrates the sucrose exporter gene of SEQ ID NO. 13. In exemplary embodiments, the sucrose exporter genes have sequence identity of about 76%, 80%, 85%, at least about 90%, and at least about 95%, 96%, 97%, 98% or 99% to SEQ ID NO. 13

C. Urea

Additionally, other urea cycle pathway intermediates are up-regulated and non-urea producing metabolic pathways are down-regulated or blocked in exemplary embodiments. For example, in one embodiment the urea cycle genes, i.e. CPS-1, OTC, ASS, and AS, are up-regulated. Polynucleotides encoding the genes are operably connected to an *Anabaena* PglnA promoter and the host cell is genetically engineered with the construct.

D. Long Chain Alkanes

In still another embodiment, host cells are engineered to increase production of long chain hydrocarbons such as alkanes/alkenes, i.e. C8-C18. In many embodiments with increased production of long chain hydrocarbons, secretion of the long chain hydrocarbons is also increased. *Anabaena* is innately capable of producing and secreting long-chain alkanes/alkenes. Long chain alkanes/alkenes can be produced in *Anabaena* from both the fatty acid pathway and the MEP pathway. In the fatty acid pathway, acyl-ACP reductase (AR) combined with aldehyde decarbonylase (AD) convert fatty acid to alkanes/alkenes Schirmer A, Rude M A, Li X, Popova E, del Cardayre S B. 2010. Microbial biosynthesis of alkanes. *Science.* 329(5991):559-62. In embodiments where host cells are engineered to increase production of long chain alkanes, the host cell is genetically engineered with a polynucleotide encoding AR and/or AD. Known sources of AR and AD exist in many cyanobacteria and any AR and AD gene capable of expression may be used with the disclosed embodiments. In many embodiments, the AR and/or AD genes are native Anabaena genes, i.e. native AR and/or AD are over-expressed. For example, in one embodiment the AR/AD genes will be from Anabaena cylindrica 29414 such as those demonstrated by SEQ ID NO. 14 and SEQ ID NO. 15. In other embodiments, the AR and AD genes have sequence identity of about 76%, 80%, 85%, at least about 90%, and at least about 95%, 96%, 97%, 98% or 99% to SEQ ID NO. 14 and SEQ ID NO. 15.

E. Long-Chain Hydrocarbons from Isoprenoid Biosynthesis Pathway

In still another embodiment, the host cell is engineered to increase the production of carbon-based products of interest from the native isoprenoid biosynthesis pathway, i.e. the 2-C-methyl-D-erythritol 4-phosphate (MEP) pathway. In many embodiments, excretion of the carbon-based products of interest is also increased. DMAPP and IPP, the early precursors for many carbon-based products of interest are made through MEP pathway in Anabaena. In heterotrophic organisms, DMAPP and IPP are made from precursors mainly derived from glucose through gluconeogenesis. However, as demonstrated in FIG. 4 photosynthetic organisms produce DMAPP and IPP from precursors directly synthesized from $CO_2$ via the Calvin cycle and perhaps also from photorespiration. Cyanobacteria, in addition to initiating the MEP pathway via glyceraldehyde-3-phosphate (G3P) and pyruvate, can use phosphorylated sugars directly from the Calvin cycle as precursors for entering into the MEP pathway. Due to their higher photosynthetic efficiency and greater innate MEP pathway flux for making DMAPP and IPP precursors, cyanobacteria, such as Anabaena are especially suited for engineering production of excreted carbon-based products of interest. Therefore, genetically engineering photosynthetic organisms such as Anabaena to produce MEP pathway carbon-based products of interest has greater advantages than genetically engineering heterotrophic organisms.

Figure 4:
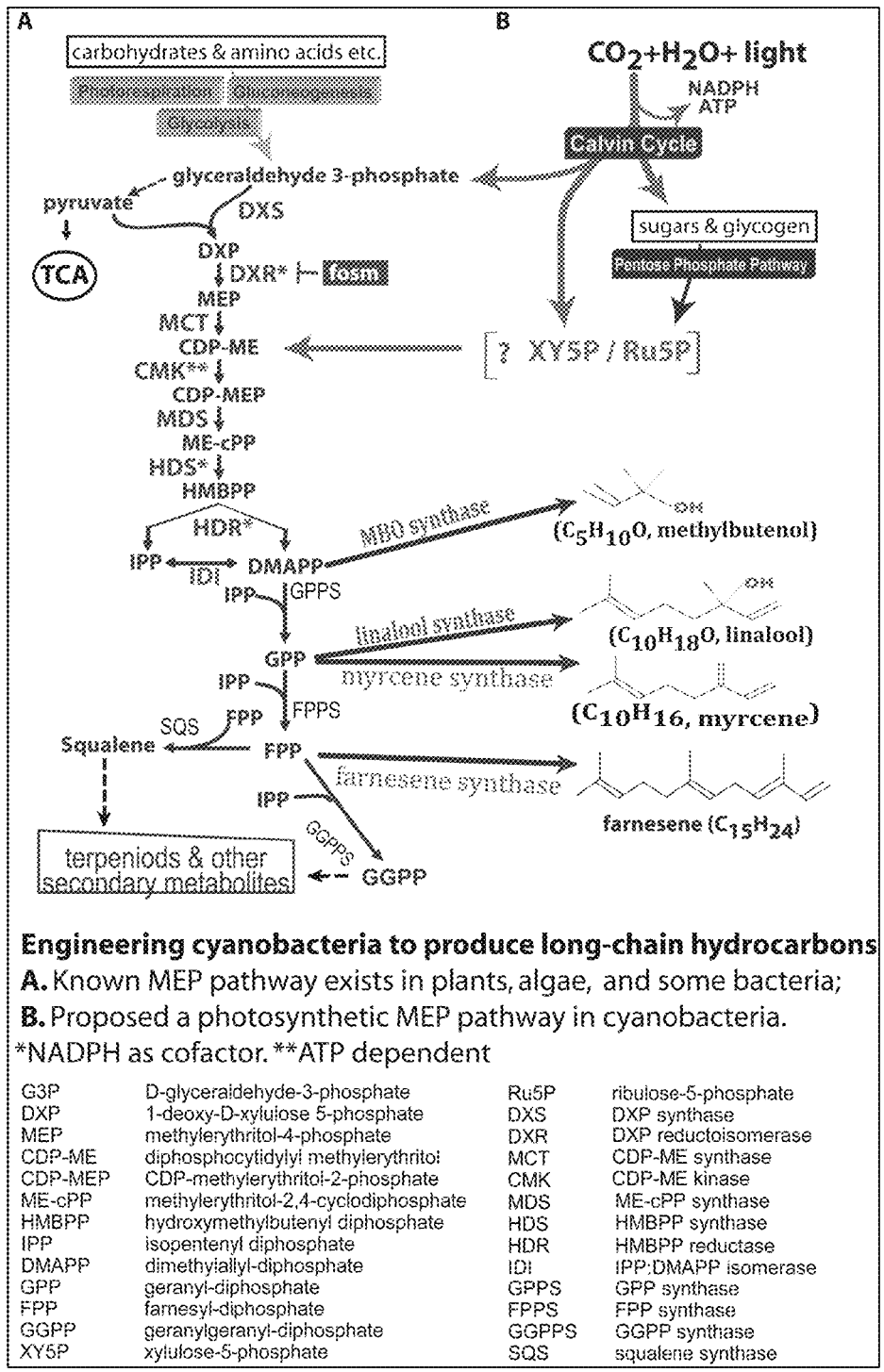
FIG. 4 shows (A) the known MEP pathway as it exists in plants, algae and some bacterial and (B) the proposed synthetic pathway in cyanobacteria.

In some embodiments, components of the MEP pathway are up-regulated to manipulate the DMAPP and IPP pool so as to maximize production of carbon-based products of interest. This up-regulation is achieved through transformation of the host by an expression vector with polynucleotides containing one or more of the eight genes of the MEP pathway. FIG. 4 and FIG. 13 show the individual components of the MEP pathway. The genes responsible for the MEP pathway include dxs, dxr, mct, cmk, mds, hds, hdr, and idi. In many cases, the MEP pathway polynucleotide expression may be constructed as a synthetic operon. This operon is fused to an Anabaena psbA promoter in pZR807 (a pNIR derivative shuttle vector) in many embodiments. In certain embodiments, the dxr, hds, and hdr are from Synechocysitis sp. PCC6803. In Synechocysitis, the corresponding genes are sll0019, slr2136, and slr0348 respectively. In another embodiment, DXS will be overexpreesed. Kuzuyama T, Takagi M, Takahashi S, Seto H.2000. Cloning and characterization of 1-deoxy-D-xylulose 5-phosphate synthase from Streptomyces sp strain CL190, which uses both the mevalonate and nonmevalonate pathways for isopentenyl diphosphate biosynthesis. J. Bacteriol. 182(4):891-7, Cordoba E, Salmi M, Leon P. 2009. Unravelling the regulatory mechanisms that modulate the MEP pathway in higher plants. J Exp Bot. 60(10):2933-43, Alper H, Fischer C, Nevoigt E, Stephanopoulos G. 2005. Tuning genetic control through promoter engineering. Proc. Natl. Acad. Sci. USA. 102:12678-83, Alper H, Stephanopoulos G. 2008. Uncovering the gene knockout landscape for improved lycopene production in E. coli. Appl. Microbiol. Biotechnol. 78:801-10. In this embodiment, to overexpress DXS, the DXS gene (alr0599) from Anabaena will be PCR amplified with primers containing restriction sites and a ribosome binding site. The resulting PCR product will be fused to a nitrate-inducible promoter Pnir and cloned into pZR807, a shuttle plasmid that can replicate both in E. coli and Anabaena. This construction will be introduced into Anabaena for overexpression of DXS.

The genes of the MEP pathway are generally placed into the operon in the pathway order, although this is not required. The genes may be flanked with restriction nuclease sites non-native to the applicable genes to make insertion and deletion of specific genes more convenient. When the restriction sites are intended to allow removal of a portion of the operon and replacement with another sequence, different restriction enzyme sites are used on each side of the portion of the operon. When the restriction sites are intended to allow removal of a portion of the operon and not be replaced, the same restriction nuclease site exists on both sides. In most embodiments, restriction nuclease sites are engineered to produce sticky-ends. Polynucleotide sequences for individual genes have engineered ribosome binding sites in many embodiments. In some instances, the genes additionally include spacer sequences for enhancing translation of target genes.

a. Linalool ($C_{10}H_{18}O$)

Linalool ($C_{10}H_{18}O$) is a carbon-based product of interest produced from the MEP pathway where the universal isoprenoid intermediate geranyl disphosphate (GPP) is converted to linalool by linalool synthase (LinS) (see FIG. 4). In these embodiments, host is genetically engineered with a polynucleotide encoding LinS such that the host cell has up-regulated production of linalool. Known sources of LinS genes exist and any LinS gene capable of being expressed may be used with the disclosed embodiments. For example, polynucleotide encoding LinS may be from a Norway Spruce. In many embodiments, the polynucleotide encoding LinS is not native to Anabaena. LinS genes such as CbLinS, McLinS, and LaLinS are well studied and contemplated for use in the disclosed embodiments.

TABLE 1

Genes required for linalool production in engineering cyanobacteria

| | Gene name | Accession No. | Km (μM) | Organism | References |
|---|---|---|---|---|---|
| linalool synthase | LaLINS | DQ263741 | 47.4 | Lavandula angustifolia | Landmann et al., 2007 |
| | Mc Lis | AY083653 | 25 | Mentha citrata | Crowell et al., 2002 |
| | CbLis | U58314 | 0.9 | Clarkia breweri | Pichersky et al., 1995 Dudareva et al., 1996 |

In exemplary embodiments, the expression vector encoding LinS includes a promoter. For example, in some embodiments, the expression vector includes an Anabaena Pnir promoter. In this embodiment the expression vector may be a shuttle vector pZR807.

In many embodiments, a host cell is genetically engineered with both polynucleotide encoding genes of the MEP pathway as well as LinS. This transformation may include a single expression vector or multiple expression vectors. In other embodiments, a LinS gene is fused to a promoter and then subcloned into an integration vector and this resulting construction pLinS is then introduced into the host cell for double homologous recombination. The double recombinants are then selected by loss of a conditional lethal gene such as sacB.

Linalool producing *Anabaena* sp. PCC7120 (pZR808) strain was deposited at the American Type Culture Collection on Feb. 27, 2012, and given accession number PTA-12832. PTA-12832 was deposited with the American Type Culture Collection (ATCC) at 10801 University Blvd., Manassas, Va. 20110-2209 (USA). The deposit was made under the provisions of the Budapest Treaty on the International Recognition of Deposited microorganisms for the Purposes of Patent Procedure and Regulations thereunder (Budapest Treaty). Maintenance of a viable culture is assured for thirty years from the date of deposit. The organism will be made available by the ATCC under the terms of the Budapest Treaty, and subject to an agreement between the Applicants and the ATCC which assures unrestricted availability of the deposited cells to the public upon the granting of patent from the instant application.

b. Methylbutenol ($C_5H_{10}O$)

Another carbon-based product of interest produced by an intermediate product from the MEP pathway, i.e. DMAPP, is methylbutenol (MBO). Methylbutenol is produced in the MEP pathway when DMAPP is converted to methylbutenol by methylbutenol synthase (MboS). In these embodiments, host cell is genetically engineered with a polynucleotide encoding MboS such that the host cell has up-regulated production of methylbutenol. Known sources of MboS exist and any MboS gene capable of being expressed may be used with the disclosed embodiments. In certain embodiments, the polynucleotide encoding MboS is from *Pinus sabiniana* and listed as below. Gray D W, Breneman S R, Topper L A, Sharkey T D. 2011, Biochemical characterization and homology modeling of methylbutenol synthase and implications for understanding hemiterpene synthase evolution in plants. J Biol. Chem. 286(23):20582-90. SEQ ID NO. 16. In other embodiments, MboS have sequence identity of about 76%, 80%, 85%, at least about 90%, and at least about 95%, 96%, 97%, 98% or 99% to SEQ ID NO. 16.

In many embodiments, a host cell is genetically engineered with both polynucleotide encoding genes of the MEP pathway as well as MboS. This transformation may include a single expression vector or multiple expression vectors.

c. Myrcene ($C_{10}H_{16}$)

Yet another carbon-based product of interest produced from an intermediate of the MEP pathway is myrcene. Myrcene is produced in the MEP pathway where the universal isoprenoid intermediate geranyl disphosphate (GPP) is converted to myrcene by myrcene synthase (MyrS) Dudareva N, Martin D, Kish C M, Kolosova N, Gorenstein N, Fäldt J, Miller B, Bohlmann J. 2003. (E)-beta-ocimene and myrcene synthase genes of floral scent biosynthesis in snapdragon: function and expression of three terpene synthase genes of a new terpene synthase subfamily. *Plant Cell.* 15(5):1227-41. Martin D M, Fäldt J, Bohlmann J. 2004. Functional characterization of nine Norway Spruce TPS genes and evolution of gymnosperm terpene synthases of the TPS-d subfamily. *Plant Physiol.* 135(4):1908-27. Lijima Y, Davidovich-Rikanati R, Fridman E, Gang D R, Bar E, Lewinsohn E, Pichersky E. 2004. The biochemical and molecular basis for the divergent patterns in the biosynthesis of terpenes and phenylpropenes in the peltate glands of three cultivars of basil. *Plant Physiol.* 136(3):3724-36. No MyrS gene is founded in cyanobacterial genomes. In these embodiments, host is genetically engineered with a polynucleotide encoding MyrS such that the host cell has increased production of myrcene. Known sources of MyrS exist and any MyrS gene capable of being expressed may be used with the disclosed embodiments. In many embodiments, the polynucleotides encoding MyrS may be chosen from the organisms listed in the following table:

TABLE 2

Myrcene synthase gene required for engineering cyanobacteria to produce myrcence

| Gene Name | Accession No. | Organism |
|---|---|---|
| Myrcene synthase (MyrS) Ag.2. | U87908 | *Abies grandis* |
| Amale20 | AA041726 | *Antirrhinum majus* |
| PaTPs-Myr | AY473626 | Norway Spruce |
| MyS | AAV63791 | *Ocimum basilicum* |
| Ama0c15 | AY195608 | Snapdragon |

In many embodiments, a host cell is genetically engineered with both polynucleotide encoding genes of the MEP pathway as well as MyrS. This transformation may include a single expression vector or multiple expression vectors.

d. Farnesene ($C_{15}H_{24}$)

And still another carbon based product of interest produced by MEP pathway is farnesene. Farnesene is produced in the MEP pathway by conversion of geranyl-diphosphate (GPP) to farnesyl-diphosphate (FPP) by FPP synthase (FPPS). Subsequently, FPP is converted to farnesene by farnesene synthase (FarS) Maruyama T, Ito M, Honda G. 2001. Molecular cloning, functional expression and characterization of (E)-beta farnesene synthase from Citrus junos. *Biol. Pharm. Bull.* 24:1171-5 and Picaud S, Brodelius M, Brodelius P E. 2005. Expression, purification and characterization of recombinant (E)-beta-farnesene synthase from *Artemisia* annua. Phytochemistry. 66(9):961-7. In *Anabaena*, only a putative FPPS gene exists and no FarS gene is found. In these embodiments, host cell is genetically engineered with a polynucleotide encoding FPPS and FarS such that the host cell has increased production of farnesene. Known sources of FPPS and FarS exist and any FPPS or FarS gene capable of being expressed may be used with the disclosed embodiments. In many embodiments, the polynucleotides encoding FPPS and FarS are chosen from the organisms listed in the following table:

TABLE 3

Genes required for engineering cyanobacteria to produce farnesene

| | Gene Name | Accession No. | Organism |
|---|---|---|---|
| Farnesyl diphosphate synthase (FPPS) | FDSI | AY308477 | *Artemisis tridentate* |
| | TbFPPS | AY158342 | *Trypanosoma brucei* |
| | FPS2 | NP_974565 | *Arabidopsis thaliana* |
| | ispA | NP-414955 | *E. coli* K-12 |
| | pFPS2 | U20771 | *Lupinus albus* |
| Farnesene synthase (FarS) | AFS1 | AY182241 | *Malus domestica* |
| | CJFS | AF374462 | *Citrus junos* |
| | CmTpsDul | EU158099 | *Cucumis melo* L. |
| | FS | AY835398 | *Artemisis annua* |
| | PmeTPS4 | AY906867 | *Pseudotsuga menziesii* |

In certain embodiments, the FPPS and FarS will be from the same organism. In other embodiments, the constructs will include FPPS and FarS from different organisms. In many embodiments, a host cell is genetically engineered with both polynucleotide encoding genes of the MEP pathway as well as FPPS and FarS. This transformation may include a single expression vector or multiple expression vectors.

In most embodiments, production of carbon-based products of interest is further optimized. For example, photosynthesis is optimized and/or competing metabolic pathways are blocked or inactivated. Photosynthetic rates can be increased by the over-expression of RuBisCo and RuBisCo activase. Hudson G S, Evans J R, von Caemmerer S, Arvidsson Y B, Andrews T J. 1992. Reduction of Ribulose-1,5-Bisphosphate Carboxylase/Oxygenase Content by Antisense RNA Reduces Photosynthesis in Transgenic Tobacco Plants. *Plant Physiol.* 98, 294-302 and Peterhansel C, Niessen M, Kebeish R M. 2008. Metabolic engineering towards the enhancement of photosynthesis. *Photochem. Photobiol.* 84:1317-23. In embodiments where host cells producing the carbon-based products of interest using $CO_2$ and $H_2O$ as the starting material, the hosts are often additionally genetically engineered with polynucleotides encoding RuBisCo and RuBisCo activase.

When carbon-based products of interest are produced from the MEP pathway, glycogen synthesis, which competes with the MEP metabolic pathway in the host is down-regulated or blocked in many embodiments. Glycogen synthesis is down-regulated or blocked by the down-regulation or block of ADP-glucose pyrophosphorylase (ADP-GPPase) activity. Pyruvate dehydrogenase (PDH) is additionally or alternatively blocked in these embodiments. GPP flux may be optimized by downregulating farnesyl-disphosphate synthase (FPPS). Additionally, in certain embodiments genes for the tolerance of a host cell to economically relevant concentrations of the carbon based product of interest are included. In embodiments where competing carbon pathways are blocked or partially inactivated, this may be done using any method known in the art. For example, enzymes in competing pathways can be knocked out or have their activity blocked or reduced. In certain embodiments, unmarked gene deletion created by double-crossover to delete target genes is used to delete *Anabaena* genes.

EXAMPLES

The invention may be further clarified by reference to the following Examples, which serve to exemplify some of the embodiments and not to limit the invention in any way. The experiments were performed using the methodology described below.

Example 1

Conjugation

Briefly, host cells are harvested by centrifugation and re-suspended in medium at a concentration of about $2-5\times10^8$ cells per ml. To one ml of this cell solution is added the appropriate construct to a final concentration of 2 μg/ml. Host cells are incubated in the dark for 8 hours followed by a 16 h light incubation prior to plating on media plates containing antibiotic. Plates are incubated under standard growth conditions (30° C. light intensity of 100 μmol photons m-2 S-1). Antibiotic resistant colonies are chosen and the genetically modified host cells are grown, bubbling with air at 30° C. and a light intensity of 100 μmol photons m-2 S-1 in liquid medium containing an appropriate antibiotic

Example 2

Culture Growth

Transgenic cyanobacter cultures will be grown in liquid BG-11 medium in a lighted shaker (Innova 44R, New Brunswick Scientific) at 30° C. and 150 μmol photons m-2 s-1. One week-old cultures will be used to re-inoculate 500 ml Erlenmeyer flasks containing 100 ml liquid BG11, which will then be incubated at 30° C. and 150 μmol photons m-2 s-1 with a 24 h lighting set. Heterotrophic cultures will be supplemented with 100 g L-1 glucose. Samples will be collected at regular intervals and analyzed for product production, as well as chlorophyll content. Chlorophyll will be measured with a spectrophotometer.

Example 3

Ethanol Production

Both $pdc_{zm}$ and $adhB_{zm}$ coding regions, with an engineered optimized SD sequence (ribosome binding site) immediately upstream of their initiation codons were PCR amplified from pLOI295, which contains both $pdc_{zm}$ and $adhB_{zm}$ in an artificial operon. See Ingram L O et al. 1987 Genetic Engineering of Ethanol Production in *Escherichia coli. Appl. Environ. Microbiol.* 53(10):2420-5. The DNA fragment was fused to *Anabaena* nitrate inducible promoter (nir) in shuttle vector. See Desplancq, D. et al. 2005 Combining inducible protein overexpression with NMR-grade triple isotope labeling in the cyanobacterium *Anabaena* sp. PCC 7120. *Biotechniques.* 39:405-11 and Frias et al. 2000. Activation of the *Anabaena* nir operon promoter requires both NtcA (CAP family) and NtcB (LysR family) transcription factors. *Mol. Microbiol.* 38:613-25. This construct, named pZR672, was introduced into *Anabaena* by conjugation. See Zhou, R. and Wolk, C. P. 2002. Identification of an akinete marker gene in *Anabaena variabilis. J Bacteriol.* 184:2529-32; Wolk, C. P. et al. 1984 Construction of shuttle vectors capable of conjugative transfer from *Escherichia coli* to nitrogen-fixing filamentous cyanobacteria, *Proc Natl Acad Sci USA.* 81:1561-5; and Zhou, R. and Wolk, C. P. 2003. A two-component system mediates developmental regulation of biosynthesis of a heterocyst polysaccharide. *J Biol. Chem.* 278:19939-46. Genetically engineered hosts were selected in a nitrate-minus (AA/8 medium) Kan plate. Tests of ethanol production were done using well established protocols. Current ethanol productivity, as shown in FIG. 3 is about 13.8 mg/liter/h/$1.0A_{700}$.

Example 4

Sucrose Production

Figure 11:
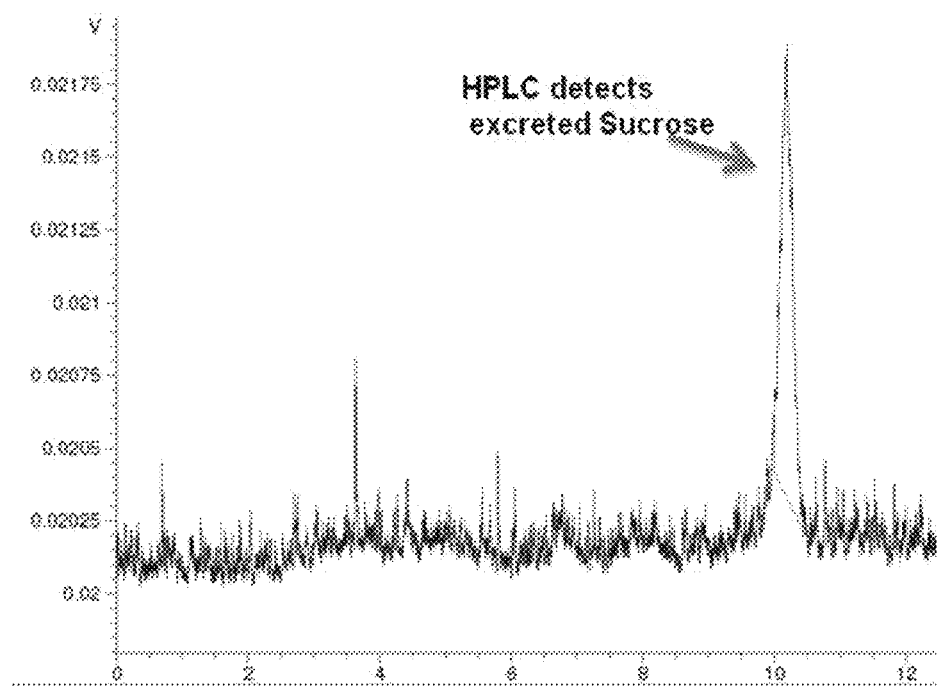
FIG. 11 demonstrates sucrose produced by Anabaena sp. PCC7120.

Both sps and spp coding regions, with an engineered optimized SD sequence (ribosome binding site) immediately upstream of their initiation codons will be PCR amplified from sugarcane/sugar beet cDNA. The DNA fragment will be fused to *Anabaena* nitrate inducible promoter (nir) in shuttle vector pNIR. This construct will be introduced into *Anabaena* by conjugation. See Wolk, C. P. et al. 1984 Construction of shuttle vectors capable of conjugative transfer from *Escherichia coli* to nitrogen-fixing filamentous cyanobacteria, *Proc Natl Acad Sci USA.* 81:1561-5. Genetically transformed *Anabaena* will be selected in a nitrate-containing (AA/8 N medium) Km plate. Antibiotic resistant colonies will be chosen and the genetically modified host cells will be grown, bubbling with air at 30° C. and a light intensity of 100 μmol photons m-2 s-1 in liquid medium containing appropriate antibiotic. HPLC tests of sucrose production by *Anabaena* sp. PCC7120 are demonstrated in FIG. 11.

Figure 5:
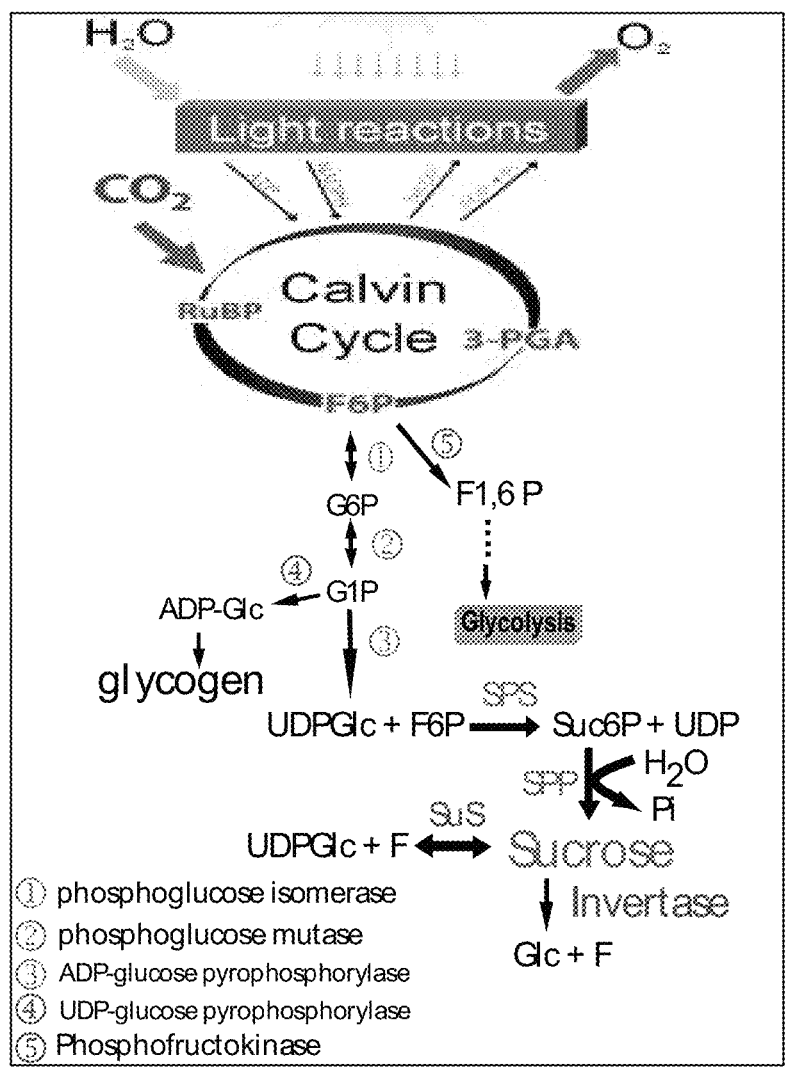
FIG. 5 shows metabolic pathway for photosynthetic production of sucrose.

Sucrose degradation will be reduced by blocking invertases and sucrose synthases (SuS) (see FIG. 5). Two genes, alr0819 and alr1521, coding for *Anabaena* invertases and two genes, all4985 and all1059, coding for sucrose synthases will be inactivated in a double crossover approach, such as the one demonstrated in Zhou, R., Wolk, C. P. 2003. A two-component system mediates developmental regulation of biosynthesis of a heterocyst polysaccharide. *J. Biol. Chem.* 278:19939-46. Phosphofructokinase (PFK) will also be down-regulated in certain embodiments. The genes coding for *Anabaena* PFK, all7335 and alr1919, will be down-regulated or knocked out using a double crossover approach or through expression of the antisense gene. In one embodiment, one PFK gene will be knocked out, while the other will be down-regulated. In another embodiment, both PFK genes will be down-regulated.

Example 5

Figure 10:
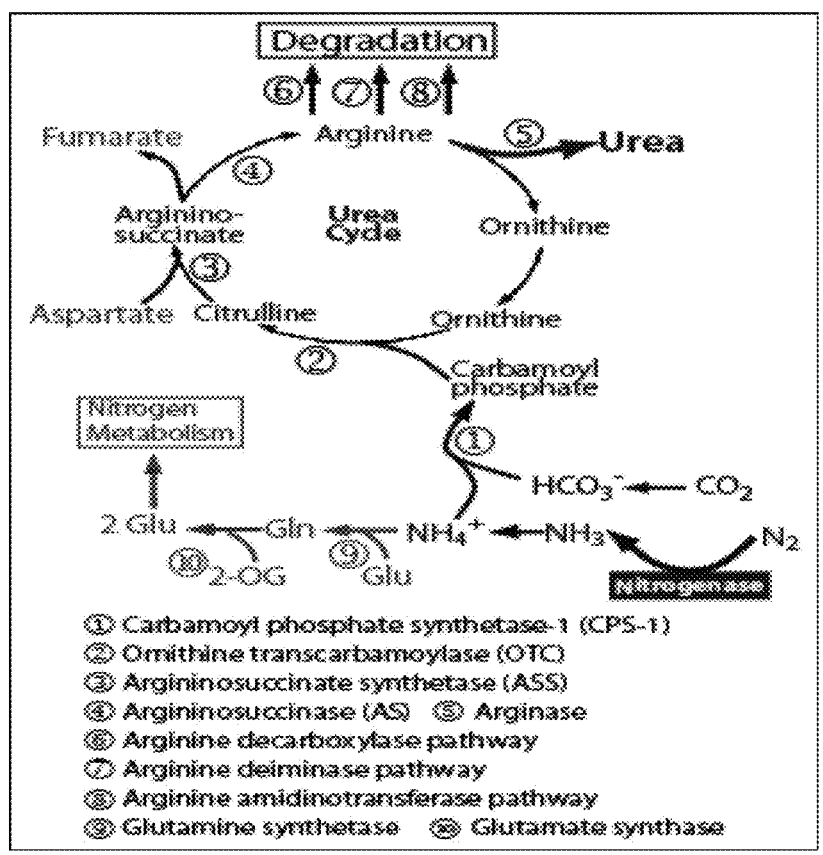
FIG. 10 shows engineering $N_2$-fixing cyanobacteria to produce urea using solar energy.

Urea Production a. Create a novel strain with more closely spaced heterocysts. It is known that overexpression of patA gene in *Anabaena* or inactivation of patN gene in *Nostoc punctiforme* led to more closely spaced single heterocysts, with an average vegetative cell interval of 3.2 cells (Meeks, J. C., E. L. Campbell, M. L. Summers, and F. C. Wong. 2002. Cellular Differentiation in the cyanobacterium *Nostoc punctiforme*. *Arch. Microbiol.* 178: 395-403; Liang J, Scappino L, Haselkorn R. 1992. The patA gene product, which contains a region similar to CheY of *Escherichia coli*, controls heterocyst pattern formation in the cyanobacterium *Anabaena* 7120. *Proc. Natl. Acad. Sci. USA.* 89(12):5655-9)). A novel *Anabaena* will be created by combining over-expression of patA and inactivation of patN in *Anabaena*. This patA+patN− strain will serve as a model strain for further genetic modification to produce urea.

b. Manipulate nitrogen flux in patA+patN− strain. *Anabaena* will be engineered to convert surplus ammonia to urea. All 5 human homologous genes required for urea cycle are found in the *Anabaena* genome, as well as genes coding for urea transporters. The urea cycle's final reaction is arginase-catalyzed hydrolysis of arginine to yield urea and regenerate ornithine (FIG. 10). Initially an authentic arginase LeARG1 from tomato will be overexpressed in patA$^+$patN$^−$ strain and inactivate its urease Alr3666. Chen H, McCaig B C, Melotto M, He S Y, Howe G A. 2004, Regulation of plant arginase by wounding, jasmonate, and the phytotoxin coronatine. *J. Biol. Chem.* 279(44):45998-6007. To overexpress these genes in *Anabaena*, the *Anabaena* PglnA, a constitutively strong promoter that functions in both vegetative cells and heterocysts, will be fused to urea cycle genes and followed by overexpression of them in the patA$^+$patN$^−$ urease$^−$LeARG$^+$ strain.

c. Shut down the cyanophycin synthesis in patA$^+$patN$^−$ urease$^−$LeARG$^+$ strain. Cyanophycin synthesis will be blocked and fixed nitrogen will be redirected to excreted urea. A single gene, all3879, encoding cyanophycin synthetase will be knocked out by a double crossover approach (Zhou R, Wolk C P. 2003. A two-component system mediates developmental regulation of biosynthesis of a heterocyst polysaccharide. *J. Biol. Chem.* 278:19939-46).

The disclosed genetically engineered urea-producing *Anabaena* strains will be grown in a liquid $N_2$-medium (Bg11$_0$ medium which contains no combined nitrogen) in a lighted shaker (Innova 44R, New Brunswick Scientific) at 30° C. and 150 μmol photons m-2 s-1. One week-old cultures will be used to re-inoculate 4-liter Erlenmeyer flasks containing 1000 ml liquid BG11$_0$, which will then be incubated at 30° C. and 150 μmol photons m-2 s-1 with a 24 h lighting set. Samples will be collected at regular intervals (24 h) and analyzed for urea production. Urea excreted in the culture fluid will be measured by HPLC. Results will be used to guide further genetic manipulations.

Example 6

Long Chain Hydrocarbon Production and Isoprenoid Biosynthetic Pathway Product Production a. Linalool Production To engineer *Anabaena* to produce linalool, CbLinS, McLinS, and LaLinS (see Table 1) will be transferred into *Anabaena*. The coding region of the three genes, with N-terminal plastid targeted sequence deletion, was cloned immediately downstream of the engineered translation initiation sequence (Shine-Dalargno sequence) under a dual promoter (Pnir/PsbA) in shuttle vector pZR807, a pNIR derived plasmid that replicates in *Anabaena*. Each construct will be introduced into *Anabaena* by conjugation.

Transgenic *Anabaena* cultures will be grown in liquid BG-11 medium in a lighted shaker (Innova 44R, New Brunswick Scientific) at 30° C. and 150 μmol photons m-2 s-1. One week-old cultures will be used to re-inoculate 500 ml Erlenmeyer flasks containing 100 ml liquid BG11, which will then be incubated at 30° C. and 150 μmol photons m-2 s-1 with a 24 h lighting set. Heterotrophic cultures will be supplemented with 100 g L-1 glucose. Samples will be collected at regular intervals and analyzed for linalool production, as well as chlorophyll content.

Figure 6:
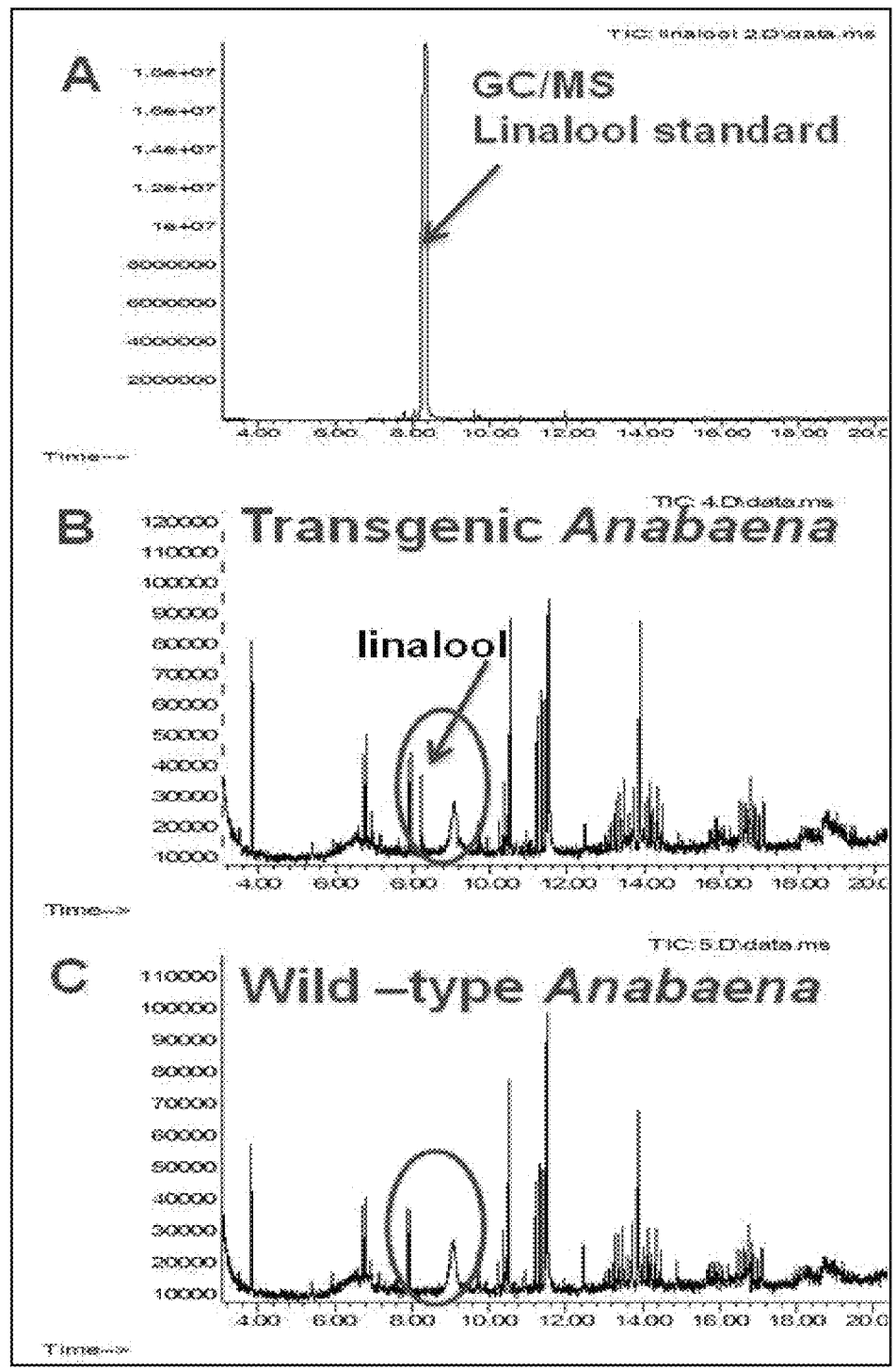
FIG. 6 shows (B) linalool production in genetically engineered Anabaena as measured by GC/MS and (C) native production of long chain alkanes/alkenes in wild-type Anabaena sp. PCC7120.
Figure 7:
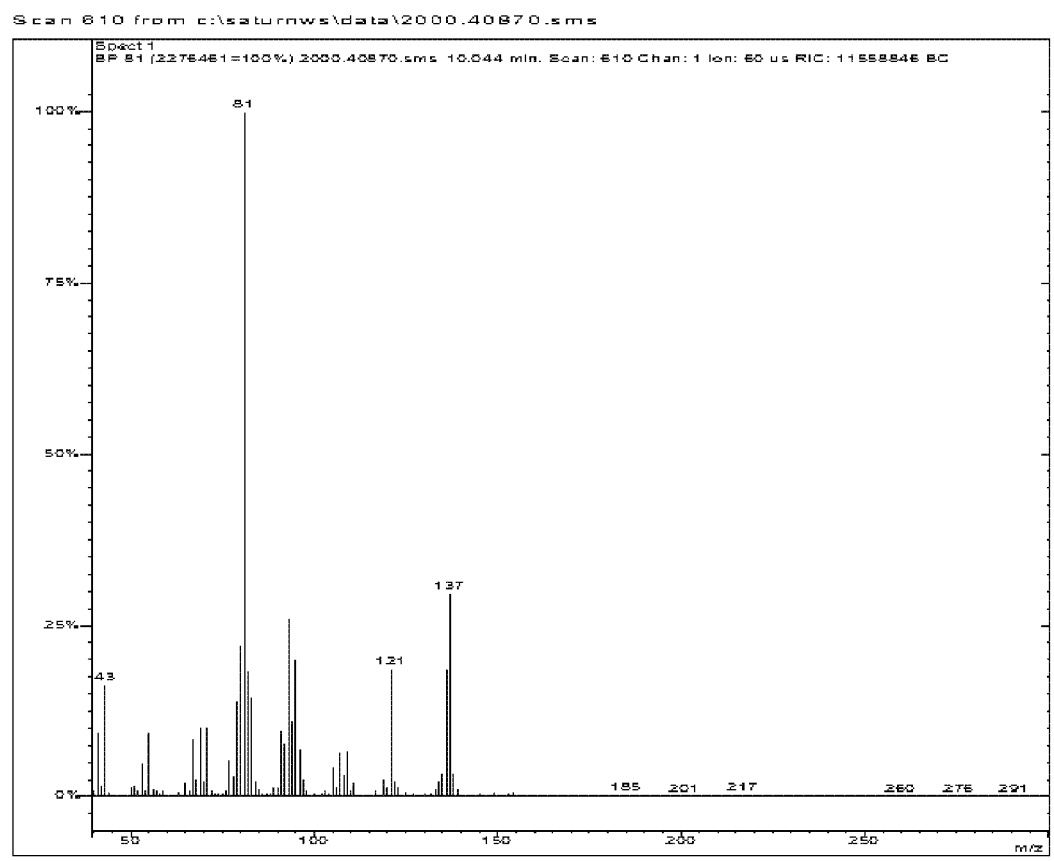
FIG. 7 shows mass spectra for linalool ($C_{10}H_{18}O$) standard.
Figure 8:
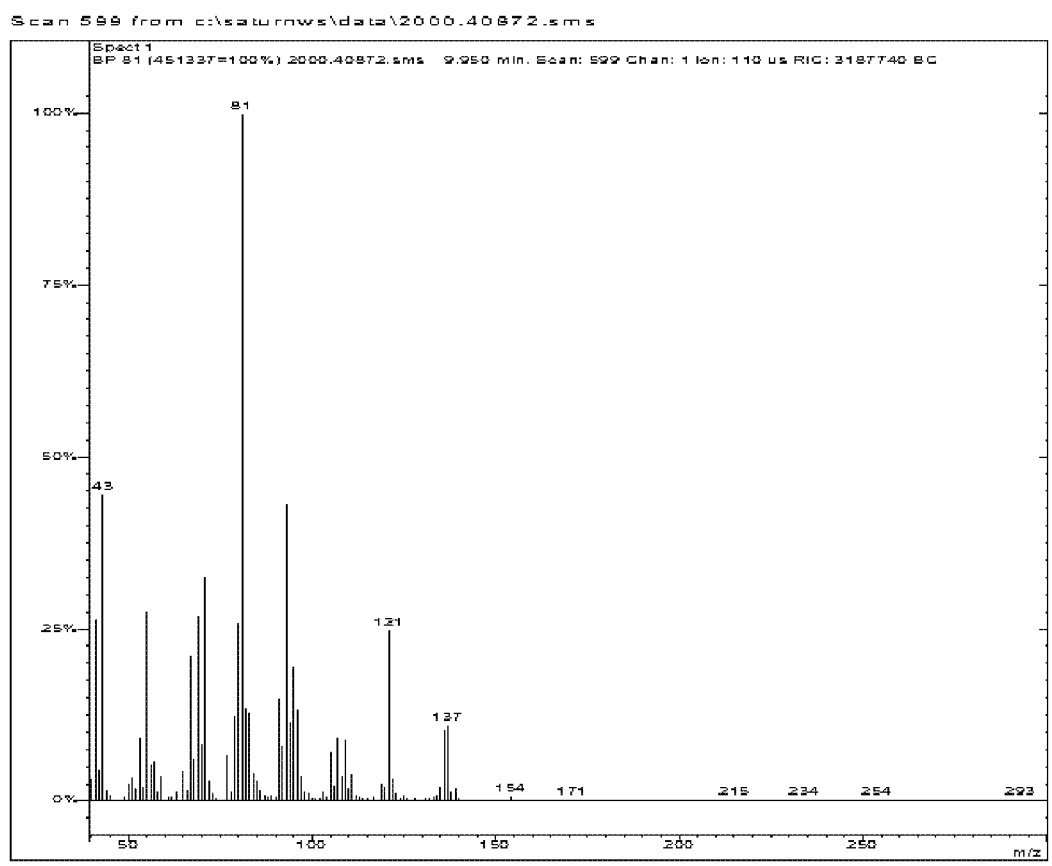
FIG. 8 shows mass spectra for linalool produced by engineered Anabaena.
Figure 9:
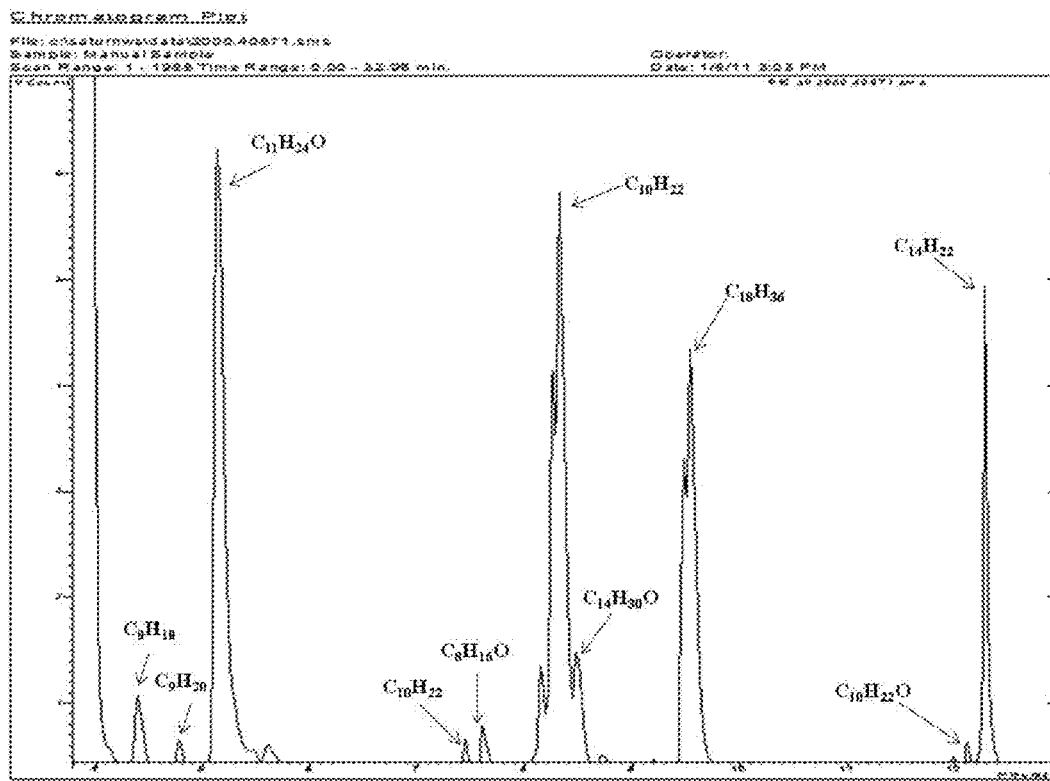
FIG. 9 shows hydrocarbons produced by Anabaena cylindrica 29414.

Chlorophyll will be measured with a spectrophotometer. To measure volatile linalool, 2 ml culture samples will be placed a sealed 20 ml headspace tubes, and incubated at 30° C. for 2 hour. Volatiles will be sampled with a headspace sampler and measured by GC-MS. Linalool will be identified by comparison with genuine standard from GC-Standard grade liquid linalool. Linalool emission rates will be calculated in nmol g-1 chlorophyll h-1 over 2 hour incubation by headspace analysis. Linalool in the culture fluid will be measured by HPLC. Results will be used to guide further genetic manipulations. FIG. 6. demonstrates the production of linalool in transgenic *Anabaena*.

b. Methylbutenol Production

To engineer *Anabaena* to produce methylbutenol (MBO), methylbutenol synthase (MboS) will be transferred into *Anabaena*. The coding region of the MboS, with N-terminal plastid targeted sequence deletion, was cloned immediately downstream of the engineered translation initiation sequence (Shine-Dalargno sequence) under a dual promoter (Pnir/PsbA) in shuttle vector pZR807, a pNIR derived plasmid that replicates in *Anabaena*. Each construct was introduced into *Anabaena* by conjugation. Genetically engineered MBO-producing *Anabaena* strains (see above) will be grown in a liquid Bg11 medium which contains combined nitrogen in a lighted shaker (Innova 44R, New Brunswick Scientific) at 30° C. and 150 μmol photons m-2 s-1. One week-old cultures will be used to re-inoculate 4-liter Erlenmeyer flasks containing 1000 ml liquid BG11, which will then be incubated at 30° C. and 150 μmol photons m-2 s-1 with a 24 h lighting set. Samples will be collected at regular intervals (24 h) and analyzed for MBO production. MBO excreted in the culture fluid will be measured by HPLC or GC/MS. Results will be used to guide further genetic manipulations.

c. Myrcene Production

To engineer *Anabaena* to produce myrcene, three MyrS genes in Table 2, i.e. ag2, ama0c15, and AtTPS 10 will be transferred into the host. The coding region of the three genes, with N-terminal plastid targeted sequence deletion will be cloned immediately downstream of the engineered translation initiation sequence (Shine-Dalgarno sequence) under *Anabaena* psbA promoter (PpsbA) in shuttle vector pZR807, a plasmid that replicates in *Anabaena* and bears kanamycin resistance gene $Kan^R$. The constructs will be individually introduced into the host by conjugation. Genetically engineered *Anabaena* will be selected in a nitrate-containing AA/N medium agar plate supplemented with kanamycin sulfate. In certain experiments, a nitrate-inducible promoter will be used to replace the PpsbA promoter. In some experiments, an epitope tagged MyrS will be designed. The construct allows the 3' of MyrS gene in frame to link to $FLAG_2$-$His_6$ epitope tag engineered into the pZR807 vector once the MyrS gene stop codon is removed. Genetically engineered myrcene-producing *Anabaena* strains will be grown as described for linalool-producing strain. The myrcene production will measured by GC/MS as described for linalool measurement.

d. Farnesene Production

FPPS and FarS genes from *Artmisia* will be constructed as an operon under the control of the psbA promoter in shuttle vector pZR807. The construct will be individually introduced into *Anabaena* by conjugation. Genetically engineered *Anabaena* will be selected in a nitrate-containing AA/N medium agar plate supplemented with kanamycin sulfate. In certain embodiments, a nitrate-inducible promoter will be used to replace the PpsbA promoter. In some embodiments, an epitope tagged FarS will be designed. The construct allows the 3' of FarS gene in frame to link to $FLAG_2$-$His_6$ epitope tag engineered into the pZR807 vector once the FarS gene stop codon is removed. Farnesene produced by engineered *Anabaena* will be measured as described for linalool measurement.

Example 7

Optimization of Production of Carbon Based Products of Interest a. RuBisCo/RuBisCo Activase The native RuBisCo genes rbcL/S (slr009/slr0012) and the putative RuBisCo activase (slr0011) gene will be over-expressed in hosts producing the carbon based product of interest. These three genes will be PCR amplified and fused to a strong *Anabaena* promoter PpsbA and subcloned into a shuttle vector for conjugation.

FBP/SBPase will be over-expressed to boost RUBP levels. Hosts producing carbon based products of interest will be genetically engineered with FBP/SBPase from *Synechococcus* PCC794. See Miyagawa Y, Tamoi M, Shigeoka S. 2001. Overexpression of a cyanobacterial fructose-1,6-/sedoheptulose-1,7-bisphosphatase in tobacco enhances photosynthesis and growth. *Nat. Biotechnol.* 19(10):965-9 and Tamoi M, Nagaoka M, Miyagawa Y, Shigeoka 5.2006. Contribution of fructose-1,6-bisphosphatase and sedoheptulose-1,7-bisphosphatase to the photosynthetic rate and carbon flow in the Calvin cycle in transgenic plants. *Plant Cell Physiol.* 47(3): 380-90 b. ADP-GPPase

Figure 12:
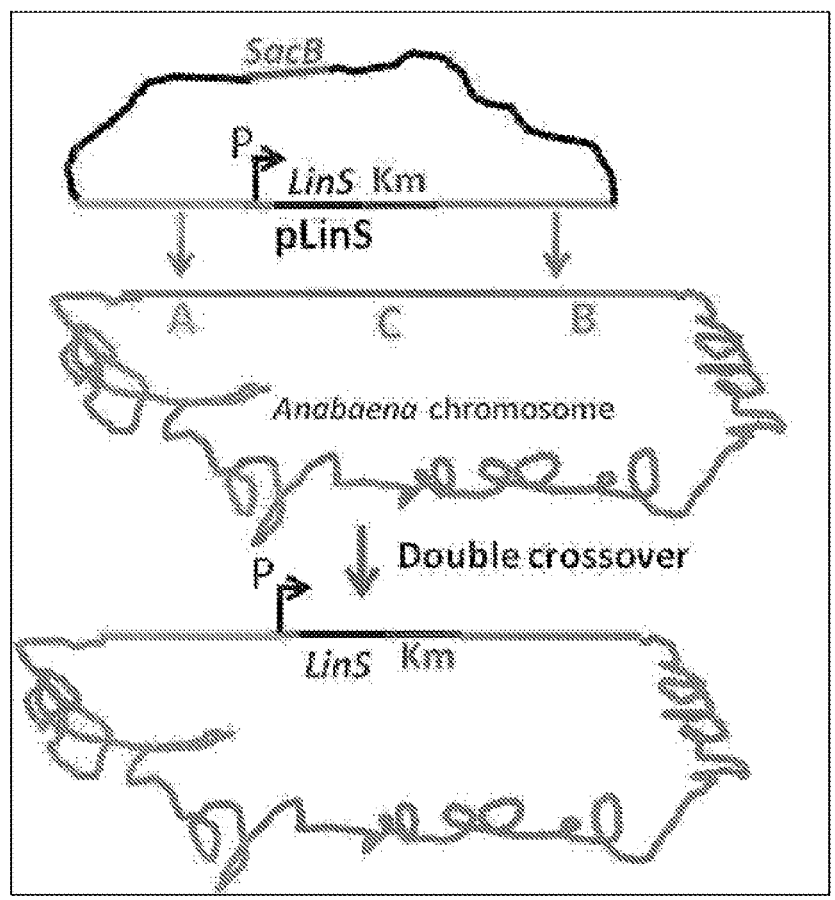
FIG. 12 illustrates a LinS gene integrated to Anabaena chromosome at loci A and B.

ADP-GPPase will be inactivated or deleted in certain genetically engineered *Anabaena*. ADP-GPPase may be inactivated using a double crossover knockout approach. This approach is well documented in Zhou R and Wolk C P. 2002 Identification of an akinete marker gene in *Anabaena variabilis*. *J. Bacteriol*. 184:2529-32 and Zhou R and Wolk C P 2003 A two-component system mediates developmental regulation of biosynthesis of a heterocyst polysaccharide. *J. Biol. Chem.* 278:19939-46. In *Anabaena*, the ADP-GPPase gene is all4645. As shown in FIG. 12, for example, LinS gene fused to *Anabaena* promoter is subcloned to an integration vector (fragment A and B are from *Anabaena* chromosome) and this resulting construction pLinS is then introduced to *Anabaena* for double homologous recombination at loci A and B of *Anabaena* chromosome. The double recombinants will be selected on the sucrose/Km plate by losing the conditional lethal gene sacB in the vector portion (Cai Y P, Wolk C P. 1990. Use of a conditionally lethal gene in *Anabaena* sp. strain PCC 7120 to select for double recombinants and to entrap insertion sequences. *J. Bacteriol*. June; 172(6):3138-3145). The completely segregated double recombinants will be further verified by diagnostic PCR. Thus, the LinS/Km cassette from integration plasmid pLinS has replaced the gene all4645 (pink C in FIG. 12) in the double recombinants. In this example, gene all4645 has been deleted from *Anabaena* chromosome.

c. PDH

*Anabaena* PDH will be inactivated in some experiments. The internal fragment of alr4745, one of the three genes encoding *Anabaena* PDH multienzyme complex, will be amplified from *Anabaena* 7120 genomic DNA and cloned into pRL278, a plasmid designed for conjugative transfer into cyanobacteria. The alr4745 will be knocked out according to the method disclosed in Zhou R and Wolk C P 2003 A two-component system mediates developmental regulation of biosynthesis of a heterocyst polysaccharide. *J. Biol. Chem.* 278:19939-46.

d. GGPPS/SQS

If a decrease in the FPP flux to terpeniods is desired, geranylgeranyl diphosphate synthase (GGPPS) and/or squalene synthase (SQS) expression will be down-regulated. SQS and or GGPS antisense sequences will be used to down-regulate GGPPS and/or SQS. The construct may additionally include an inducible promoter. The inducible promoter will be inducible by nitrate in many experiments. The gppS antisense sequence will be cloned downstream of a nitrate-inducible promoter and conjugatively transferred into hosts genetically engineered to produce target products. Down-regulating GPPS will be achieved by inducing antisense RNA expression with the addition of nitrate to the growth medium when cell density reaches the maximum.

e. FPPS

GPP flux will be optimized by down-regulating farnesyl-disphosphate synthase (FPPS). FPPS will be over-expressed in the antisense direction under an inducible promoter. The fppS antisense sequence will be cloned downstream of a nitrate-inducible promoter and conjugatively transferred into hosts genetically engineered to produce linalool or myrcene. Down-regulating FPPS is achieved by inducing antisense RNA expression with the addition of nitrate to the growth medium when cell density reaches the maximum.

f. Pyruvate Synthesis

Figure 2:
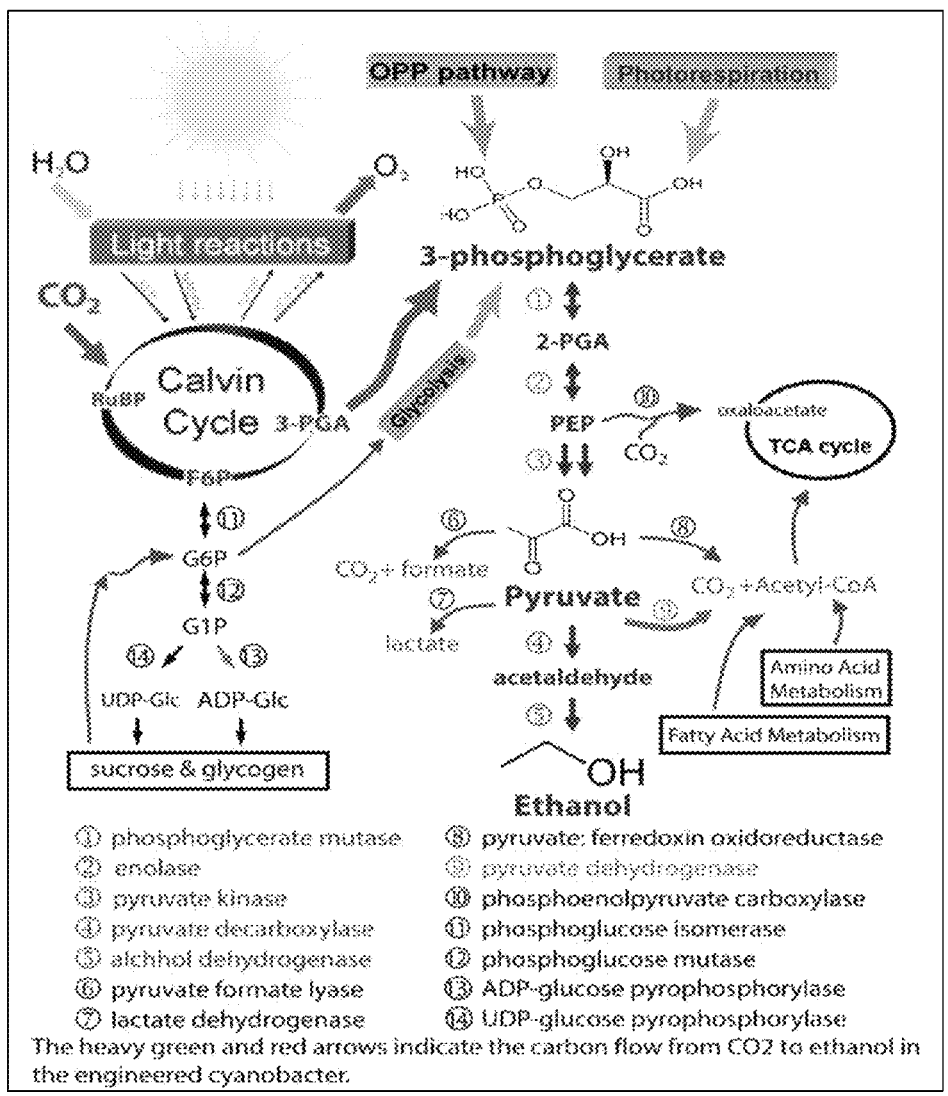
FIG. 2 demonstrates the modified cyanobacterial carbon metabolic pathway for production of ethanol.

Pyruvate synthesis will be increased by over-expressing phosphoglycerate mutase, enolase, and pyruvate kinase (See FIG. 2). Three robust genes from *Z. mobilis* and from *S. cerevisiae* will be constructed as an artificial operon and fused to a PsbA1 promoter and then cloned into an integrative vector to insert the enzyme genes within the coding region of alr4745 (encoding PDH-E3). This allows for increased synthesis of pyruvate while concurrently inactivating PDH.

GP3 flux may be altered by over-expressing certain rate-limiting enzymes. The DXS gene (alr0599) from *Anabaena* and the *Arabidopsis* IDI gene (AT5G16440) will be PCR amplified with primers containing restriction sites and a ribosome binding site. The resulting PCR product will be fused to a nitrate-inducible promoter Pnir and cloned into pZR807.

All of the references cited herein are incorporated by reference in their entireties.

From the above discussion, one skilled in the art can ascertain the essential characteristics of the invention, and without departing from the spirit and scope thereof, can make various changes and modifications of the embodiments to adapt to various uses and conditions. Thus, various modifications of the embodiments, in addition to those shown and described herein, will be apparent to those skilled in the art from the foregoing description. Such modifications are also intended to fall within the scope of the appended claims.

What is claimed is:

1. A composition comprising an *Anabaena* spp. genetically engineered with at least one recombinant polynucleotide expression construct, wherein the at least one recombinant polynucleotide expression construct comprises a nucleotide sequence encoding at least one enzyme, wherein the at least one enzyme increases production of a carbon based product of interest by the genetically engineered *Anabaena* spp. following expression of the polynucleotide expression construct, wherein said *Anabaena* spp. is ethanol producing *Anabaena* sp. PCC7120 (pZR672) strain deposited under ATCC accession number PTA-12833 or is linalool producing *Anabaena* sp. PCC7120 (pZR808) strain deposited under ATCC accession number PTA-12832.

2. The composition of claim 1 wherein the *Anabaena* spp. is *Anabaena* PCC7120 (pZR672) strain deposited under ATCC accession number PTA-12833.

3. The composition of claim 1, wherein the *Anabaena* spp. is linalool producing *Anabaena* sp. PCC7120 (pZR808) strain deposited under ATCC accession number PTA-12832.

4. The composition of claim 1 wherein the *Anabaena* spp. has an up-regulated 2-C-methyl-D-erythritol 4-phosphate (MEP) pathway.

5. The composition of claim 4 wherein the up-regulated MEP pathway is up-regulated by expressing at least one gene responsible for control of the MEP pathway in the *Anabaena* spp.

6. The composition of claim 1 wherein the at least one recombinant polynucleotide expression construct further comprises a nucleotide sequence encoding ribulose-1,5-bisphosphate carboxylase/oxygenase (RuBisCo).

7. The composition of claim 6 wherein the at least one recombinant polynucleotide expression construct comprising a nucleotide sequence encoding RuBisCo, further comprises a nucleotide sequence encoding RuBisCo activase.

8. The composition of claim 1 wherein the carbon based product of interest is ethanol.

9. The composition of claim 1 wherein the *Anabaena* spp. is combined with a photoautotrophic liquid media, and optionally, wherein said media contains no combined nitrogen.

10. The composition of claim 1 wherein the carbon based product of interest is linalool ($C_{10}H_{18}O$).

* * * * *

```
                            SEQUENCE LISTING

<160> NUMBER OF SEQ ID NOS: 16

<210> SEQ ID NO 1
<211> LENGTH: 590
<212> TYPE: DNA
<213> ORGANISM: Anabaena sp.
<220> FEATURE:
<221> NAME/KEY: misc_feature
<223> OTHER INFORMATION: Anabaena Pnir promoter sequence

<400> SEQUENCE: 1
gatctagcta ctcattagtt aagtgtaatg cagaaaacgc atattctcta ttaaacttac      60
gcattaatac gagaattttg tagctactta tactatttta cctgagatcc cgacataacc     120
ttagaagtat cgaaatcgtt acataaacat tcacacaaac cacttgacaa atttagccaa     180
tgtaaaagac tacagtttct ccccggttta gttctagagt taccttcagt gaaacatcgg     240
cggcgtgtca gtcattgaag tagcataaat caattcaaaa taccctgcgg gaaggctgcg     300
ccaacaaaat taaatatttg gtttttcact attagagcat cgattcatta atcaaaaacc     360
ttacccccca gccccttcc cttgtaggga agtgggagcc aaactcccct ctccgcgtcg     420
gagcgaaaag tctgagcgga ggtttcctcc gaacagaact tttaaagaga gaggggttgg     480
gggagaggtt ctttcaagat tactaaattg ctatcactag acctcgtaga actagcaaag     540
actacgggtg gattgatctt gagcaaaaaa actttatgag aacgaattcg                590

<210> SEQ ID NO 2
<211> LENGTH: 161
<212> TYPE: DNA
<213> ORGANISM: Anabaena sp.
<220> FEATURE:
<221> NAME/KEY: misc_feature
<223> OTHER INFORMATION: Anabaena psbA1 promoter sequence

<400> SEQUENCE: 2
ggattcccaa agatagggg aataattaac attaagaatt attaattcat gggtttttag       60
tctagtaaat ttgcgtgaat tcatgtaaat tttatgagac aggcgcaagt ctaaaaaaag     120
cgtctgaatt aatctgcaca aatccaaagc aatcataaaa a                         161

<210> SEQ ID NO 3
<211> LENGTH: 402
<212> TYPE: DNA
<213> ORGANISM: Anabaena sp.
<220> FEATURE:
<221> NAME/KEY: misc_feature
<223> OTHER INFORMATION: Anabaena PrbcL promoter sequence

<400> SEQUENCE: 3
gttaacaaaa cgtttaaaac tttatgtaat aacaaattta aatatgtaag ttaagaactt      60
tcaaagaata acttatgcca tttcttgata tattgtgaga caagttacaa attacgtggt     120
gtgcaatttt ttcatcttgc gctgattact ctactaaata tccgtcaagt aaattggctc     180
ttagctcgtc tcctgtcaat aaaggaggtc ggcaagagtg cagaagcggg aatgtgtgaa     240
aactaaccca attcattaaa taccccgaaa tatagggggaa tcatctcata ctttccgtaa    300
```

```
accgcgaagg tcgtgaaggg ataaaagcaa tttagtgggt gagaagaaca gataaaaaag    360
aattttttaa ctatggcaag aggaaaaagt aaaagcgtta ac                       402
```

<210> SEQ ID NO 4
<211> LENGTH: 244
<212> TYPE: DNA
<213> ORGANISM: E. coli
<220> FEATURE:
<221> NAME/KEY: misc_feature
<223> OTHER INFORMATION: E. coli tac promoter sequence

<400> SEQUENCE: 4

```
cgactgcacg gtgaccaatg cttctggcgt caggcagcca tcggaagctg tggtatggct    60
gtgcaggtcg taaatcactg cataattcgt gtcgctcaag cgcactccc gttctggata    120 atgtttttg cgccgacatc ataacggttc tggcaaatat tctgaaatga gctgttgaca    180
attaatcatc ggctcgtata atgtgtggaa ttgtgagcgg ataacaattt cacacaggaa    240
acag                                                                244
```

<210> SEQ ID NO 5
<211> LENGTH: 568
<212> TYPE: PRT
<213> ORGANISM: Zymomonas mobilis subsp. mobilis CP4
<220> FEATURE:
<221> NAME/KEY: misc_feature
<223> OTHER INFORMATION: Pyruvate Decarboxylase

<400> SEQUENCE: 5

```
Met Ser Tyr Thr Val Gly Thr Tyr Leu Ala Glu Arg Leu Val Gln Ile
 1               5                  10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Val Val Thr Tyr Ser Val Gly Ala Leu Ser Ala
 65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220
```

```
Ala Glu Glu Ala Ala Val Lys Phe Ala Asp Ala Leu Gly Gly Ala Val
225                 230                 235                 240

Ala Thr Met Ala Ala Lys Ser Phe Phe Pro Glu Glu Asn Pro His
            245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
        290                 295                 300

Val Leu Ala Glu Pro Arg Ser Val Val Asn Gly Val Arg Phe Pro
305                 310                 315                 320

Ser Val His Leu Lys Asp Tyr Leu Thr Arg Leu Ala Gln Lys Val Ser
                325                 330                 335

Lys Lys Thr Gly Ala Leu Asp Phe Phe Lys Ser Leu Asn Ala Gly Glu
            340                 345                 350

Leu Lys Lys Ala Ala Pro Ala Asp Pro Ser Ala Pro Leu Val Asn Ala
        355                 360                 365

Glu Ile Ala Arg Gln Val Glu Ala Leu Leu Thr Pro Asn Thr Thr Val
    370                 375                 380

Ile Ala Glu Thr Gly Asp Ser Trp Phe Asn Ala Gln Arg Met Lys Leu
385                 390                 395                 400

Pro Asn Gly Ala Arg Val Glu Tyr Glu Met Gln Trp Gly His Ile Gly
                405                 410                 415

Trp Ser Val Pro Ala Ala Phe Gly Tyr Ala Val Gly Ala Pro Glu Arg
            420                 425                 430

Arg Asn Ile Leu Met Val Gly Asp Gly Ser Phe Gln Leu Thr Ala Gln
        435                 440                 445

Glu Val Ala Gln Met Val Arg Leu Lys Leu Pro Val Ile Ile Phe Leu
    450                 455                 460

Ile Asn Asn Tyr Gly Tyr Thr Ile Glu Val Met Ile His Asp Gly Pro
465                 470                 475                 480

Tyr Asn Asn Ile Lys Asn Trp Asp Tyr Ala Gly Leu Met Glu Val Phe
                485                 490                 495

Asn Gly Asn Gly Gly Tyr Asp Ser Gly Ala Gly Lys Gly Leu Lys Ala
            500                 505                 510

Lys Thr Gly Gly Glu Leu Ala Glu Ala Ile Lys Val Ala Leu Ala Asn
        515                 520                 525

Thr Asp Gly Pro Thr Leu Ile Glu Cys Phe Ile Gly Arg Glu Asp Cys
    530                 535                 540

Thr Glu Glu Leu Val Lys Trp Gly Lys Arg Val Ala Ala Ala Asn Ser
545                 550                 555                 560

Arg Lys Pro Val Asn Lys Leu Leu
                565
```

<210> SEQ ID NO 6
<211> LENGTH: 383
<212> TYPE: PRT
<213> ORGANISM: Zymomonas mobilis CP4
<220> FEATURE:
<221> NAME/KEY: misc_feature
<223> OTHER INFORMATION: Alcohol Dehydrogenase II

<400> SEQUENCE: 6

```
Met Ala Ser Ser Thr Phe Tyr Ile Pro Phe Val Asn Glu Met Gly Glu
1               5                   10                  15
```

```
Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
            35                  40                  45

Lys Gln Val Ala Asp Leu Leu Lys Ala Gln Gly Ile Asn Ser Ala Val
 50                  55                  60

Tyr Asp Gly Val Met Pro Asn Pro Thr Val Thr Ala Val Leu Glu Gly
 65                  70                  75                  80

Leu Lys Ile Leu Lys Asp Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
            115                 120                 125

Pro Ala Leu Pro Leu Met Ser Ile Asn Thr Thr Ala Gly Thr Ala Ser
130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
            195                 200                 205

Thr Pro Ile Thr Asp Ala Cys Ala Leu Lys Ala Ala Ser Met Ile Ala
210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
                245                 250                 255

Ala Ser Leu Gly Tyr Val His Ala Met Ala His Gln Leu Gly Gly Tyr
            260                 265                 270

Tyr Asn Leu Pro His Gly Val Cys Asn Ala Val Leu Leu Pro His Val
            275                 280                 285

Leu Ala Tyr Asn Ala Ser Val Val Ala Gly Arg Leu Lys Asp Val Gly
290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350

Leu Ala Asp His Ala Leu Lys Asp Ala Cys Ala Leu Thr Asn Pro Arg
            355                 360                 365

Gln Gly Asp Gln Lys Glu Val Glu Glu Leu Phe Leu Ser Ala Phe
370                 375                 380

<210> SEQ ID NO 7
<211> LENGTH: 1045
<212> TYPE: PRT
<213> ORGANISM: Beta vulgaris subsp. vulgaris
<220> FEATURE:
<221> NAME/KEY: misc_feature
<223> OTHER INFORMATION: Sugar beet sucrose-phosphate synthase (SPS)
```

```
<400> SEQUENCE: 7

Met Ala Gly Asn Asp Trp Ile Asn Ser Tyr Leu Glu Ala Ile Leu Asp
1               5                   10                  15

Val Gly Pro Gly Leu Asp Asp Ala Lys Ser Ser Leu Leu Arg Glu
            20                  25                  30

Arg Gly Arg Phe Ser Pro Thr Arg Tyr Phe Val Glu Val Ile Thr
        35                  40                  45

Gly Phe Asp Glu Thr Asp Leu His Arg Ser Trp Val Arg Ala Gln Ala
    50                  55                  60

Thr Arg Ser Pro Gln Glu Arg Asn Thr Arg Leu Glu Asn Met Cys Trp
65                  70                  75                  80

Arg Ile Trp Asn Leu Ala Arg Gln Lys Lys Gln Leu Glu Asn Glu Glu
                85                  90                  95

Ala Gln Arg Lys Thr Lys Arg Arg Met Glu Leu Glu Arg Gly Arg Arg
            100                 105                 110

Glu Ala Thr Ala Asp Met Ser Glu Asp Leu Ser Glu Gly Leu Lys Asp
            115                 120                 125

Ile Ser Ala His Gly Asp Ser Thr Arg Pro Arg Leu Pro Arg Ile Asn
130                 135                 140

Ser Leu Asp Ala Met Glu Thr Trp Ile Ser Gln Gln Lys Glu Lys Lys
145                 150                 155                 160

Leu Tyr Leu Val Leu Ile Ser Leu His Gly Leu Ile Arg Gly Glu Asn
                165                 170                 175

Met Glu Leu Gly Arg Asp Ser Asp Thr Gly Gln Val Lys Tyr Val
            180                 185                 190

Val Glu Leu Ala Arg Ala Leu Gly Ser Met Pro Gly Val Tyr Arg Val
            195                 200                 205

Asp Leu Leu Thr Arg Gln Val Ser Ser Pro Asp Val Asp Trp Ser Tyr
            210                 215                 220

Gly Glu Pro Thr Glu Met Leu Asn Pro Arg Asp Ser Asn Gly Phe Asp
225                 230                 235                 240

Asp Asp Asp Asp Glu Met Gly Glu Ser Ser Gly Ala Tyr Ile Val Arg
            245                 250                 255

Ile Pro Phe Gly Pro Arg Asp Lys Tyr Ile Ala Lys Glu Glu Leu Trp
            260                 265                 270

Pro Tyr Ile Pro Glu Phe Val Asp Gly Ala Leu Asn His Ile Val Gln
            275                 280                 285

Met Ser Lys Val Leu Gly Glu Gln Ile Gly Ser Gly Glu Thr Val Trp
290                 295                 300

Pro Val Ala Ile His Gly His Tyr Ala Asp Ala Gly Asp Ser Ala Ala
305                 310                 315                 320

Leu Leu Ser Gly Gly Leu Asn Val Pro Met Leu Leu Thr Gly His Ser
            325                 330                 335

Leu Gly Arg Asp Lys Leu Glu Gln Leu Leu Lys Gln Gly Arg Met Ser
            340                 345                 350

Lys Asp Asp Ile Asn Asn Thr Tyr Lys Ile Met Arg Arg Ile Glu Ala
            355                 360                 365

Glu Glu Leu Ser Leu Asp Ala Ser Glu Ile Val Ile Thr Ser Thr Arg
            370                 375                 380

Gln Glu Ile Glu Glu Gln Trp His Leu Tyr Asp Gly Phe Asp Pro Val
385                 390                 395                 400

Leu Glu Arg Lys Leu Arg Ala Arg Met Lys Arg Gly Val Ser Cys Tyr
            405                 410                 415
```

```
Gly Arg Phe Met Pro Arg Met Val Val Ile Pro Pro Gly Met Glu Phe
            420                 425                 430

Asn His Ile Val Pro His Glu Gly Asp Met Asp Gly Glu Thr Glu Glu
            435                 440                 445

Thr Glu Glu His Pro Thr Ser Pro Asp Pro Pro Ile Trp Ala Glu Ile
450                 455                 460

Met Arg Phe Phe Ser Lys Pro Arg Lys Pro Met Ile Leu Ala Leu Ala
465                 470                 475                 480

Arg Pro Asp Pro Lys Lys Asn Ile Thr Thr Leu Val Lys Ala Phe Gly
                485                 490                 495

Glu Cys Arg Pro Leu Arg Glu Leu Ala Asn Leu Thr Leu Ile Met Gly
                500                 505                 510

Asn Arg Asp Gly Ile Asp Glu Met Ser Ser Thr Ser Ser Ser Val Leu
            515                 520                 525

Leu Ser Val Leu Lys Leu Ile Asp Gln Tyr Asp Leu Tyr Gly Gln Val
            530                 535                 540

Ala Tyr Pro Lys His His Lys Gln Ala Asp Val Pro Glu Ile Tyr Arg
545                 550                 555                 560

Leu Ala Ala Lys Thr Lys Gly Val Phe Ile Asn Pro Ala Phe Ile Glu
                565                 570                 575

Pro Phe Gly Leu Thr Leu Ile Glu Ala Ala Ala His Gly Leu Pro Met
            580                 585                 590

Val Ala Thr Lys Asn Gly Gly Pro Val Asp Ile Gln Arg Val Leu Asp
            595                 600                 605

Asn Gly Leu Leu Val Asp Pro His Glu Gln Gln Ser Ile Ala Thr Ala
610                 615                 620

Leu Leu Lys Leu Val Ala Asp Lys Gln Leu Trp Thr Lys Cys Gln Gln
625                 630                 635                 640

Asn Gly Leu Lys Asn Ile His Leu Tyr Ser Trp Pro Glu His Ser Lys
                645                 650                 655

Thr Tyr Leu Ser Arg Ile Ala Ser Ser Arg Gln Arg Gln Pro Gln Trp
            660                 665                 670

Gln Arg Ser Ser Asp Glu Gly Leu Asp Asn Gln Glu Pro Glu Ser Pro
            675                 680                 685

Ser Asp Ser Leu Arg Asp Ile Lys Asp Ile Ser Leu Asn Leu Glu Val
            690                 695                 700

Leu Val Arg Pro Glu Lys Arg Val Lys Thr Leu Lys Ile Leu Gly Leu
705                 710                 715                 720

Met Thr Lys Ala Asn Ser Arg Met Leu Leu Cys Ser Trp Ser Asn Gly
                725                 730                 735

Val His Lys Met Leu Arg Lys Ala Arg Phe Ser Asp Lys Val Asp Gln
            740                 745                 750

Ala Ser Ser Lys Tyr Pro Ala Phe Arg Arg Lys Leu Ile Tyr Val
            755                 760                 765

Ile Ala Val Asp Gly Asp Tyr Glu Asp Gly Leu Phe Asp Ile Val Arg
            770                 775                 780

Arg Ile Phe Asp Ala Ala Gly Lys Glu Lys Ile Glu Gly Ser Ile Gly
785                 790                 795                 800

Phe Ile Leu Ser Thr Ser Tyr Ser Met Pro Glu Ile Gln Asn Tyr Leu
            805                 810                 815

Leu Ser Lys Gly Phe Asn Leu His Asp Phe Asp Ala Tyr Ile Cys Asn
            820                 825                 830
```

-continued

```
Ser Gly Ser Glu Leu Tyr Tyr Ser Leu Asn Ser Glu Ser Asn
        835                 840                 845

Ile Ile Ala Asp Ser Asp Tyr His Ser His Ile Glu Tyr Arg Trp Gly
850                 855                 860

Gly Glu Gly Leu Arg Arg Thr Leu Leu Arg Trp Ala Ala Ser Ile Thr
865                 870                 875                 880

Glu Lys Asn Gly Glu Asn Glu Glu Gln Val Ile Thr Glu Asp Glu Glu
                885                 890                 895

Val Ser Thr Gly Tyr Cys Phe Ala Phe Lys Ile Lys Asn Gln Asn Lys
                900                 905                 910

Val Pro Pro Thr Lys Glu Leu Arg Lys Ser Met Arg Ile Gln Ala Leu
                915                 920                 925

Arg Cys His Val Ile Tyr Cys Gln Asn Gly Ser Lys Met Asn Val Ile
        930                 935                 940

Pro Val Leu Ala Ser Arg Ser Gln Ala Leu Arg Tyr Leu Tyr Val Arg
945                 950                 955                 960

Trp Gly Val Glu Leu Ser Lys Met Val Val Phe Val Gly Glu Cys Gly
                965                 970                 975

Asp Thr Asp Tyr Glu Gly Leu Leu Gly Gly Val His Lys Thr Val Ile
                980                 985                 990

Leu Lys Gly Val Ser Asn Thr Ala  Leu Arg Ser Leu His  Ala Asn Arg
            995                 1000                1005

Ser Tyr  Pro Leu Ser His Val  Val Ser Leu Asp Ser  Pro Asn Ile
        1010                1015                1020

Gly Glu  Val Ser Lys Gly Cys  Ser Ser Ser Glu Ile  Gln Ser Ile
        1025                1030                1035

Val Thr  Lys Leu Ser Lys Ala
        1040                1045

<210> SEQ ID NO 8
<211> LENGTH: 1060
<212> TYPE: PRT
<213> ORGANISM: Saccharum hybrid cultivar ROC22
<220> FEATURE:
<221> NAME/KEY: misc_feature
<223> OTHER INFORMATION: Sugarcane sucrose phosphate synthase (SPS)

<400> SEQUENCE: 8

Met Ala Gly Asn Asp Trp Ile Asn Ser Tyr Leu Glu Ala Ile Leu Asp
1               5                   10                  15

Ala Gly Gly Ala Ala Gly Glu Ile Ser Ala Ala Gly Ser Gly Gly
            20                  25                  30

Gly Gly Asp Gly Thr Ala Gly Glu Lys Arg Asp Lys Ser Ser Leu Met
        35                  40                  45

Leu Arg Glu Arg Gly Arg Phe Asn Pro Ala Arg Tyr Phe Val Glu Glu
    50                  55                  60

Val Ile Ser Gly Phe Asp Glu Thr Asp Leu Tyr Lys Thr Trp Val Arg
65                  70                  75                  80

Thr Ser Ala Met Arg Ser Pro Gln Glu Arg Asn Thr Arg Leu Glu Asn
                85                  90                  95

Met Ser Trp Arg Ile Trp Asn Leu Ala Arg Lys Lys Gln Ile Lys
                100                 105                 110

Gly Glu Glu Ala Ser Arg Leu Ser Lys Arg Arg Met Glu Leu Glu Lys
            115                 120                 125

Ala Arg Gln Tyr Ala Ala Thr Asp Leu Ser Glu Asp Leu Ser Glu Gly
        130                 135                 140
```

```
Glu Lys Gly Glu Thr Asn Asn Glu Pro Ser Ile His Asp Glu Ser Met
145                 150                 155                 160

Arg Thr Arg Met Pro Arg Ile Gly Ser Thr Asp Ala Ile Glu Thr Trp
            165                 170                 175

Ala Asn Gln His Lys Asp Lys Leu Tyr Ile Val Leu Ile Ser Ile
                180                 185                 190

His Gly Leu Ile Arg Gly Glu Asn Met Glu Leu Gly Arg Asp Ser Asp
            195                 200                 205

Thr Gly Gly Gln Val Lys Tyr Val Val Glu Leu Ala Arg Ala Leu Gly
210                 215                 220

Ser Thr Pro Gly Val Tyr Arg Val Asp Leu Leu Thr Arg Gln Ile Ser
225                 230                 235                 240

Ala Pro Asp Val Asp Trp Ser Tyr Gly Glu Pro Thr Glu Met Leu Ser
                245                 250                 255

Pro Ile Ser Ser Glu Asn Phe Gly His Glu Leu Gly Glu Ser Ser Gly
            260                 265                 270

Ala Tyr Ile Val Arg Ile Pro Phe Gly Pro Arg Asp Lys Tyr Ile Pro
            275                 280                 285

Lys Glu His Leu Trp Pro His Ile Gln Glu Phe Val Asp Gly Ala Leu
290                 295                 300

Val His Ile Met Gln Met Ser Lys Val Leu Gly Glu Gln Ile Gly Ser
305                 310                 315                 320

Gly Gln Pro Val Trp Pro Val Val Ile His Gly His Tyr Ala Asp Ala
                325                 330                 335

Gly Asp Ser Ala Ala Leu Leu Ser Gly Ala Leu Asn Val Pro Met Val
            340                 345                 350

Phe Thr Gly His Ser Leu Gly Arg Asp Lys Leu Glu Gln Ile Leu Lys
            355                 360                 365

Gln Gly Arg Gln Thr Arg Asp Glu Ile Asn Ala Thr Tyr Lys Ile Met
370                 375                 380

Arg Arg Ile Glu Ala Glu Glu Leu Cys Leu Asp Thr Ser Glu Ile Ile
385                 390                 395                 400

Ile Thr Ser Thr Arg Gln Glu Ile Glu Gln Trp Gly Leu Tyr Asp
                405                 410                 415

Gly Phe Asp Leu Thr Met Ala Arg Lys Leu Arg Ala Arg Ile Lys Arg
            420                 425                 430

Gly Val Ser Cys Phe Gly Arg Tyr Met Pro Arg Met Ile Ala Ile Pro
            435                 440                 445

Pro Gly Met Glu Phe Ser His Ile Ala Pro His Asp Val Asp Leu Asp
            450                 455                 460

Ser Glu Glu Gly Asn Glu Asp Gly Ser Gly Ser Pro Asp Pro Ile
465                 470                 475                 480

Trp Ala Asp Ile Met Arg Phe Phe Ser Asn Pro Arg Lys Pro Met Ile
                485                 490                 495

Leu Ala Leu Ala Arg Pro Asp Pro Lys Lys Asn Ile Thr Thr Leu Val
                500                 505                 510

Lys Ala Phe Gly Glu His Arg Glu Leu Arg Asn Leu Ala Asn Leu Thr
            515                 520                 525

Leu Ile Met Gly Asn Arg Asp Val Ile Asp Glu Met Ser Ser Thr Asn
            530                 535                 540

Ala Ala Val Leu Thr Ser Val Leu Lys Leu Ile Asp Lys Tyr Asp Leu
545                 550                 555                 560
```

```
Tyr Gly Gln Val Ala Tyr Pro Lys His His Lys Gln Phe Glu Val Pro
                565                 570                 575

Asp Ile Tyr Arg Leu Ala Ala Arg Thr Lys Gly Val Phe Ile Asn Cys
            580                 585                 590

Ala Phe Ile Glu Pro Phe Gly Leu Thr Leu Ile Glu Ala Ala Ala Tyr
        595                 600                 605

Gly Leu Pro Ile Val Ala Thr Arg Asn Gly Gly Pro Val Asp Ile His
    610                 615                 620

Arg Val Leu Asp Asn Gly Ile Leu Val Asp Pro His Asn Gln Asn Glu
625                 630                 635                 640

Ile Gly Glu Ala Leu Tyr Lys Leu Val Ser Asp Lys Gln Leu Trp Thr
                645                 650                 655

Arg Cys Arg Gln Asn Gly Leu Lys Asn Ile His Gln Phe Ser Trp Pro
            660                 665                 670

Glu His Cys Lys Asn Tyr Leu Ala Arg Val Val Thr Leu Lys Pro Arg
        675                 680                 685

His Pro Arg Trp Gln Lys Asn Asp Val Ala Thr Glu Ile Ser Glu Ala
    690                 695                 700

Asp Ser Pro Glu Asp Ser Leu Arg Asp Ile His Asp Ile Ser Leu Asn
705                 710                 715                 720

Leu Gln Leu Ser Leu Asp Ser Glu Lys Ser Gly Ser Lys Glu Gly Asn
                725                 730                 735

Ser Asn Thr Val Arg Arg His Leu Glu Asp Ala Val Gln Lys Leu Ser
            740                 745                 750

Gly Val Ser Asp Ile Lys Lys Asp Gly Pro Gly Glu Asn Gly Lys Trp
        755                 760                 765

Pro Ser Leu Arg Arg Arg Lys His Ile Ile Val Ile Ala Val Asp Ser
    770                 775                 780

Val Gln Asp Ala Asp Phe Val Gln Val Ile Lys Asn Ile Phe Glu Ala
785                 790                 795                 800

Ser Ser Asn Glu Arg Ser Ser Gly Ala Val Gly Phe Val Leu Ser Thr
                805                 810                 815

Ala Arg Ala Ile Ser Glu Ile His Ala Leu Leu Ile Ser Gly Arg Ile
            820                 825                 830

Glu Ala Ser Asp Phe Asp Ala Phe Ile Cys Asn Ser Gly Ser Asp Leu
        835                 840                 845

Cys Tyr Pro Ser Ser Ser Glu Asp Met Leu Ser Pro Ala Glu Leu
    850                 855                 860

Pro Phe Met Ile Asp Leu Asp Tyr His Ser Gln Ile Glu Tyr Arg Trp
865                 870                 875                 880

Gly Gly Glu Gly Leu Arg Lys Thr Leu Ile Arg Trp Ala Ala Glu Lys
                885                 890                 895

Asn Asn Glu Ser Gly Gln Lys Ile Leu Val Glu Asp Glu Glu Cys Ser
            900                 905                 910

Ser Thr Tyr Cys Ile Ser Phe Lys Val Ser Asn Thr Ala Ala Ala Pro
        915                 920                 925

Pro Val Lys Glu Ile Arg Arg Thr Met Arg Ile Gln Ala Leu Arg Cys
    930                 935                 940

His Val Leu Tyr Ser His Asp Gly Ser Lys Leu Asn Val Ile Pro Val
945                 950                 955                 960

Leu Ala Ser Arg Ser Gln Ala Leu Arg Tyr Leu Tyr Ile Arg Trp Gly
                965                 970                 975

Val Glu Leu Ser Asn Ile Thr Val Ile Val Gly Glu Cys Gly Asp Thr
```

```
                    980             985             990
Asp Tyr Glu Gly Leu Gly Gly Val His Lys Thr Ile Ile Leu Lys
            995            1000            1005

Gly Ser Phe Asn Thr Ala Pro Asn Gln Val His Ala Asn Arg Ser
           1010            1015            1020

Tyr Ser Leu Gln Asp Val Val Ser Phe Glu Lys Gln Gly Ile Ser
           1025            1030            1035

Ser Ile Glu Gly Tyr Gly Pro Asp Asn Leu Lys Ser Ala Leu Arg
           1040            1045            1050

Gln Phe Gly Ile Leu Lys Asp
           1055            1060

<210> SEQ ID NO 9
<211> LENGTH: 420
<212> TYPE: PRT
<213> ORGANISM: Saccharum officinarum
<220> FEATURE:
<221> NAME/KEY: misc_feature
<223> OTHER INFORMATION: Sugarcane sucrose phosphate phosphatase(SPP)

<400> SEQUENCE: 9

Met Asp Lys Leu Ser Gly Ser Val Arg Leu Met Ile Val Ser Asp Leu
1               5                  10                  15

Asp His Thr Met Val Asp His His Asp Glu Glu Asn Leu Ser Leu Leu
            20                  25                  30

Arg Phe Gly Ala Leu Trp Glu Ser Val Tyr Cys Glu Asp Ser Leu Leu
        35                  40                  45

Val Phe Ser Thr Gly Arg Ser Pro Thr Leu Tyr Lys Glu Leu Arg Lys
    50                  55                  60

Glu Lys Pro Met Leu Thr Pro Asp Ile Thr Ile Met Ser Val Gly Thr
65                  70                  75                  80

Glu Ile Thr Tyr Gly Glu Ala Met Val Pro Asp Asp Gly Trp Glu Gln
                85                  90                  95

Tyr Leu Asn Asn Lys Trp Asp Arg Asn Ile Val Val Glu Glu Thr Ala
            100                 105                 110

Ser Phe Ser Glu Leu Lys Leu Gln Pro Glu Thr Glu Gln Arg Pro His
        115                 120                 125

Lys Val Ser Phe Leu Val Asp Lys Lys Ser Ala Gln Glu Val Ile Lys
    130                 135                 140

Ser Val Ala Glu Arg Leu Asp Lys Arg Gly Leu Asp Ala Lys Ile Ile
145                 150                 155                 160

Tyr Ser Gly Gly Gln Asp Leu Asp Ile Leu Pro Gln Gly Ala Gly Lys
                165                 170                 175

Gly Gln Ala Leu Ala Tyr Leu Leu Lys Lys Leu Ser Cys Gly Lys
            180                 185                 190

Pro Pro Asn Asn Thr Leu Val Cys Gly Asp Ser Gly Asn Asp Ala Glu
        195                 200                 205

Leu Phe Ser Ile Pro Gly Val Met Val Ser Asn Ala Gln Glu Glu Leu
    210                 215                 220

Leu Gln Trp Tyr Ala Glu Asn Ala Lys Asp Asn Pro Lys Ile Ile His
225                 230                 235                 240

Ala Asn Glu Arg Cys Ala Ala Gly Ile Ile Gln Ala Ile Gly His Phe
                245                 250                 255

Lys Leu Gly Pro Asn Ile Ser Pro Arg Asp Val Asp Phe Pro Tyr Ala
            260                 265                 270
```

-continued

```
Lys Glu Ala Ser Phe Lys Pro Ser Asp Ala Val Val Lys Phe Tyr Val
            275                 280                 285

Leu Tyr Glu Lys Trp Arg Arg Ala Glu Val Pro Lys Ser Asp Ser Val
            290                 295                 300

Ile Lys Tyr Phe Lys Asn Ile Thr His Ala Asn Gly Val Ile Ile His
305                 310                 315                 320

Pro Ala Gly Leu Glu Leu Ser Leu His Ala Ser Ile Asp Ala Leu Gly
                325                 330                 335

Ser Cys Tyr Gly Asp Lys Gln Gly Lys Lys Tyr Arg Ala Trp Val Asp
            340                 345                 350

Arg Leu Ala Ile Thr Gln Thr Gly Ser Asp Ser Trp Val Val Arg Phe
            355                 360                 365

Asp Leu Trp Glu Ser Glu Gly Asp Val Arg Val Cys Ser Leu Ser Ser
            370                 375                 380

Leu Ala Leu Val Leu Lys Ala Glu Ser Pro Glu Gly Phe Val Leu Thr
385                 390                 395                 400

His Ile Gln Lys Thr Trp Leu Asn Gly Tyr Ser Ser Gly Val Glu Gln
                405                 410                 415

Ala Phe Lys Val
            420

<210> SEQ ID NO 10
<211> LENGTH: 720
<212> TYPE: PRT
<213> ORGANISM: Synechocystis sp.
<220> FEATURE:
<221> NAME/KEY: misc_feature
<223> OTHER INFORMATION: Synechocystis sucrose phosphate synthase (SPS)

<400> SEQUENCE: 10

Met Ser Tyr Ser Ser Lys Tyr Ile Leu Leu Ile Ser Val His Gly Leu
1               5                   10                  15

Ile Arg Gly Glu Asn Leu Glu Leu Gly Arg Asp Ala Asp Thr Gly Gly
            20                  25                  30

Gln Thr Lys Tyr Val Leu Glu Leu Ala Arg Ala Leu Val Lys Asn Pro
        35                  40                  45

Gln Val Ala Arg Val Asp Leu Leu Thr Arg Leu Ile Lys Asp Pro Lys
    50                  55                  60

Val Asp Ala Asp Tyr Ala Gln Pro Arg Glu Leu Ile Gly Asp Arg Ala
65                  70                  75                  80

Gln Ile Val Arg Ile Glu Cys Gly Pro Glu Glu Tyr Ile Ala Lys Glu
                85                  90                  95

Met Leu Trp Asp Tyr Leu Asp Asn Phe Ala Asp His Ala Leu Asp Tyr
            100                 105                 110

Leu Lys Glu Gln Pro Glu Leu Pro Asp Val Ile His Ser His Tyr Ala
        115                 120                 125

Asp Ala Gly Tyr Val Gly Thr Arg Leu Ser His Gln Leu Gly Ile Pro
    130                 135                 140

Leu Val His Thr Gly His Ser Leu Gly Arg Ser Lys Arg Thr Arg Leu
145                 150                 155                 160

Leu Leu Ser Gly Ile Lys Ala Asp Glu Ile Glu Ser Arg Tyr Asn Met
                165                 170                 175

Ala Arg Arg Ile Asn Ala Glu Glu Thr Leu Gly Ser Ala Ala Arg
            180                 185                 190

Val Ile Thr Ser Thr His Gln Glu Ile Ala Glu Gln Tyr Ala Gln Tyr
        195                 200                 205
```

```
Asp Tyr Tyr Gln Pro Asp Gln Met Leu Val Ile Pro Pro Gly Thr Asp
    210                 215                 220

Leu Glu Lys Phe Tyr Pro Pro Lys Gly Asn Glu Trp Glu Thr Pro Ile
225                 230                 235                 240

Val Gln Glu Leu Gln Arg Phe Leu Arg His Pro Arg Lys Pro Ile Ile
                245                 250                 255

Leu Ala Leu Ser Arg Pro Asp Pro Arg Lys Asn Ile His Lys Leu Ile
            260                 265                 270

Ala Ala Tyr Gly Gln Ser Pro Gln Leu Gln Ala Gln Ala Asn Leu Val
        275                 280                 285

Ile Val Ala Gly Asn Arg Asp Asp Ile Thr Asp Leu Asp Gln Gly Pro
    290                 295                 300

Arg Glu Val Leu Thr Asp Leu Leu Thr Ile Asp Arg Tyr Asp Leu
305                 310                 315                 320

Tyr Gly Lys Val Ala Tyr Pro Lys Gln Asn Gln Ala Glu Asp Val Tyr
                325                 330                 335

Ala Leu Phe Arg Leu Thr Ala Leu Ser Gln Gly Val Phe Ile Asn Pro
            340                 345                 350

Ala Leu Thr Glu Pro Phe Gly Leu Thr Leu Ile Glu Ala Ala Ala Cys
        355                 360                 365

Gly Val Pro Ile Val Ala Thr Glu Asp Gly Gly Pro Val Asp Ile Ile
    370                 375                 380

Lys Asn Cys Gln Asn Gly Tyr Leu Ile Asn Pro Leu Asp Glu Val Asp
385                 390                 395                 400

Ile Ala Asp Lys Leu Leu Lys Val Leu Asn Asp Lys Gln Gln Trp Gln
                405                 410                 415

Phe Leu Ser Glu Ser Gly Leu Glu Gly Val Lys Arg His Tyr Ser Trp
            420                 425                 430

Pro Ser His Val Glu Ser Tyr Leu Glu Ala Ile Asn Ala Leu Thr Gln
        435                 440                 445

Gln Thr Ser Val Leu Lys Arg Ser Asp Leu Lys Arg Arg Thr Leu
    450                 455                 460

Tyr Tyr Asn Gly Ala Leu Val Thr Ser Leu Asp Gln Asn Leu Leu Gly
465                 470                 475                 480

Ala Leu Gln Gly Gly Leu Pro Gly Asp Arg Gln Thr Leu Asp Glu Leu
                485                 490                 495

Leu Glu Val Leu Tyr Gln His Arg Lys Asn Val Gly Phe Cys Ile Ala
            500                 505                 510

Thr Gly Arg Arg Leu Asp Ser Val Leu Lys Ile Leu Arg Glu Tyr Arg
        515                 520                 525

Ile Pro Gln Pro Asp Met Leu Ile Thr Ser Met Gly Thr Glu Ile Tyr
    530                 535                 540

Ser Ser Pro Asp Leu Ile Pro Asp Gln Ser Trp Arg Asn His Ile Asp
545                 550                 555                 560

Tyr Leu Trp Asn Arg Asn Ala Ile Val Arg Ile Leu Gly Glu Leu Pro
                565                 570                 575

Gly Leu Ala Leu Gln Pro Lys Glu Glu Leu Ser Ala Tyr Lys Ile Ser
            580                 585                 590

Tyr Phe Tyr Asp Ala Ala Ile Ala Pro Asn Leu Glu Glu Ile Arg Gln
        595                 600                 605

Leu Leu His Lys Gly Glu Gln Thr Val Asn Thr Ile Ile Ser Phe Gly
    610                 615                 620
```

```
Gln Phe Leu Asp Ile Leu Pro Ile Arg Ala Ser Lys Gly Tyr Ala Val
625                 630                 635                 640

Arg Trp Leu Ser Gln Gln Trp Asn Ile Pro Leu Glu His Val Phe Thr
            645                 650                 655

Ala Gly Gly Ser Gly Ala Asp Glu Asp Met Met Arg Gly Asn Thr Leu
            660                 665                 670

Ser Val Val Ala Asn Arg His His Glu Glu Leu Ser Asn Leu Gly
        675                 680                 685

Glu Ile Glu Pro Ile Tyr Phe Ser Glu Lys Arg Tyr Ala Ala Gly Ile
    690                 695                 700

Leu Asp Gly Leu Ala His Tyr Arg Phe Phe Glu Leu Leu Asp Pro Val
705                 710                 715                 720

<210> SEQ ID NO 11
<211> LENGTH: 244
<212> TYPE: PRT
<213> ORGANISM: Synechocystis sp.
<220> FEATURE:
<221> NAME/KEY: misc_feature
<223> OTHER INFORMATION: Synechocystis sucrose-phosphate phosphatase
      (SPP)

<400> SEQUENCE: 11

Met Arg Gln Leu Leu Ile Ser Asp Leu Asp Asn Thr Trp Val Gly
1               5                   10                  15

Asp Gln Gln Ala Leu Glu His Leu Gln Glu Tyr Leu Gly Asp Arg Arg
            20                  25                  30

Gly Asn Phe Tyr Leu Ala Tyr Ala Thr Gly Arg Ser Tyr His Ser Ala
        35                  40                  45

Arg Glu Leu Gln Lys Gln Val Gly Leu Met Glu Pro Asp Tyr Trp Leu
    50                  55                  60

Thr Ala Val Gly Ser Glu Ile Tyr His Pro Glu Gly Leu Asp Gln His
65                  70                  75                  80

Trp Ala Asp Tyr Leu Ser Glu His Trp Gln Arg Asp Ile Leu Gln Ala
                85                  90                  95

Ile Ala Asp Gly Phe Glu Ala Leu Lys Pro Gln Ser Pro Leu Glu Gln
            100                 105                 110

Asn Pro Trp Lys Ile Ser Tyr His Leu Asp Pro Gln Ala Cys Pro Thr
        115                 120                 125

Val Ile Asp Gln Leu Thr Glu Met Leu Lys Glu Thr Gly Ile Pro Val
    130                 135                 140

Gln Val Ile Phe Ser Ser Gly Lys Asp Val Asp Leu Leu Pro Gln Arg
145                 150                 155                 160

Ser Asn Lys Gly Asn Ala Thr Gln Tyr Leu Gln Gln His Leu Ala Met
                165                 170                 175

Glu Pro Ser Gln Thr Leu Val Cys Gly Asp Ser Gly Asn Asp Ile Gly
            180                 185                 190

Leu Phe Glu Thr Ser Ala Arg Gly Val Ile Val Arg Asn Ala Gln Pro
        195                 200                 205

Glu Leu Leu His Trp Tyr Asp Gln Trp Gly Asp Ser Arg His Tyr Arg
    210                 215                 220

Ala Gln Ser Ser His Ala Gly Ala Ile Leu Glu Ala Ile Ala His Phe
225                 230                 235                 240

Asp Phe Leu Ser

<210> SEQ ID NO 12
```

```
<211> LENGTH: 521
<212> TYPE: PRT
<213> ORGANISM: Zea mays
<220> FEATURE:
<221> NAME/KEY: misc_feature
<223> OTHER INFORMATION: ZmSUT1

<400> SEQUENCE: 12
```

| | | | | | | | | | | | | | | |
|---|---|---|---|---|---|---|---|---|---|---|---|---|---|---|
|Met|Ala|Arg|Gly|Asp|Gly|Glu|Leu|Glu|Leu|Ser|Val|Gly|Val|Arg|Gly|
|1| | | |5| | | | |10| | | | |15|

Thr Gly Gly Ala Ala Ala Ala Ala Asp His Val Ala Pro Ile
              20                  25                  30

Ser Leu Gly Arg Leu Ile Leu Ala Gly Met Val Ala Gly Val Gln
         35                  40                  45

Tyr Gly Trp Ala Leu Gln Leu Ser Leu Leu Thr Pro Tyr Val Gln Thr
 50                  55                  60

Leu Gly Leu Ser His Ala Leu Thr Ser Phe Met Trp Leu Cys Gly Pro
 65                  70                  75                  80

Ile Ala Gly Leu Val Val Gln Pro Leu Val Gly Leu Tyr Ser Asp Arg
                 85                  90                  95

Cys Thr Ala Arg Trp Gly Arg Arg Pro Phe Ile Leu Ile Gly Cys
            100                 105                 110

Met Leu Ile Cys Leu Ala Val Ile Val Gly Phe Ser Ser Asp Ile
            115                 120                 125

Gly Ala Ala Leu Gly Asp Thr Lys Glu His Cys Ser Leu Tyr His Gly
    130                 135                 140

Pro Arg Trp His Ala Ala Ile Val Tyr Val Leu Gly Phe Trp Leu Leu
145                 150                 155                 160

Asp Phe Ser Asn Asn Thr Val Gln Gly Pro Ala Arg Ala Met Met Ala
                165                 170                 175

Asp Leu Cys Gly His His Gly Pro Ser Ala Ala Asn Ser Ile Phe Cys
            180                 185                 190

Ser Trp Met Ala Leu Gly Asn Ile Leu Gly Tyr Ser Ser Gly Ser Thr
        195                 200                 205

Asn Asn Trp His Lys Trp Phe Pro Phe Leu Leu Thr Asn Ala Cys Cys
210                 215                 220

Glu Ala Cys Ala Asn Leu Lys Gly Ala Phe Leu Val Ala Val Val Phe
225                 230                 235                 240

Leu Val Met Cys Leu Thr Val Thr Leu Phe Phe Ala Asn Glu Val Pro
                245                 250                 255

Tyr Arg Gly Asn Gln Asn Leu Pro Thr Lys Ala Asn Gly Glu Val Glu
            260                 265                 270

Thr Glu Pro Ser Gly Pro Leu Ala Val Leu Lys Gly Phe Lys Asn Leu
        275                 280                 285

Pro Thr Gly Met Pro Ser Val Leu Val Thr Gly Leu Thr Trp Leu
        290                 295                 300

Ser Trp Phe Pro Phe Ile Leu Tyr Asp Thr Asp Trp Met Gly Arg Glu
305                 310                 315                 320

Ile Tyr His Gly Asp Pro Lys Gly Ser Asn Ala Gln Ile Ser Ala Phe
                325                 330                 335

Asp Glu Gly Val Arg Val Gly Ser Phe Gly Leu Leu Leu Asn Ser Ile
            340                 345                 350

Val Leu Gly Phe Ser Ser Phe Leu Ile Glu Pro Met Cys Arg Lys Val
        355                 360                 365

Gly Pro Arg Val Val Trp Val Thr Ser Asn Phe Met Val Cys Val Ala

```
                370             375             380
Met Ala Ala Thr Ala Leu Ile Ser Phe Trp Ser Leu Lys Asp Tyr His
385                 390                 395                 400

Gly Tyr Val Gln Asp Ala Ile Thr Ala Ser Thr Ser Ile Lys Ala Val
            405                 410                 415

Cys Leu Val Leu Phe Ala Phe Leu Gly Val Pro Leu Ala Ile Leu Tyr
            420                 425                 430

Ser Val Pro Phe Ala Val Thr Ala Gln Leu Ala Ala Thr Lys Gly Gly
            435                 440                 445

Gly Gln Gly Leu Cys Thr Gly Val Leu Asn Ile Ser Ile Val Ile Pro
            450                 455                 460

Gln Val Ile Ile Ala Leu Gly Ala Gly Pro Trp Asp Ala Leu Phe Gly
465                 470                 475                 480

Lys Gly Asn Ile Pro Ala Phe Gly Val Ala Ser Gly Phe Ala Leu Ile
            485                 490                 495

Gly Gly Val Val Gly Val Phe Leu Leu Pro Lys Ile Ser Lys Arg Gln
            500                 505                 510

Phe Arg Ala Val Ser Ala Gly Gly His
            515                 520

<210> SEQ ID NO 13
<211> LENGTH: 517
<212> TYPE: PRT
<213> ORGANISM: Saccharum hybrid cultivar Q117
<220> FEATURE:
<221> NAME/KEY: misc_feature
<223> OTHER INFORMATION: Sucrose transporter

<400> SEQUENCE: 13

Met Ala Arg Gly Asp Gly Glu Leu Glu Leu Ser Val Gly Val Arg Gly
1               5                   10                  15

Ala Gly Ala Ala Ala Asp His Val Ala Pro Ile Ser Leu Gly Arg
            20                  25                  30

Leu Ile Leu Ala Gly Met Val Ala Gly Val Gln Tyr Gly Trp Ala
        35                  40                  45

Leu Gln Leu Ser Leu Leu Thr Pro Tyr Val Gln Thr Leu Gly Leu Ser
    50                  55                  60

His Ala Leu Thr Ser Phe Met Trp Leu Cys Gly Pro Ile Ala Gly Leu
65                  70                  75                  80

Val Val Gln Pro Leu Val Gly Leu Tyr Ser Asp Arg Cys Thr Ala Arg
                85                  90                  95

Trp Gly Arg Arg Arg Pro Phe Ile Leu Thr Gly Cys Ile Leu Ile Ser
            100                 105                 110

Leu Ala Val Ile Val Val Gly Phe Ser Ser Asp Ile Gly Ala Ala Leu
            115                 120                 125

Gly Asp Thr Lys Glu His Cys Ser Leu Tyr His Gly Pro Arg Trp His
            130                 135                 140

Ala Ala Ile Val Tyr Val Leu Gly Phe Trp Leu Leu Asp Phe Ser Asn
145                 150                 155                 160

Asn Thr Val Gln Gly Pro Ala Arg Ala Met Met Ala Asp Leu Cys Gly
            165                 170                 175

His His Gly Pro Ser Ala Ala Asn Ser Ile Phe Cys Ser Trp Met Ala
            180                 185                 190

Leu Gly Asn Ile Leu Gly Tyr Ser Ser Gly Ser Thr Asn Asn Trp His
            195                 200                 205
```

```
Lys Trp Phe Pro Phe Leu Lys Thr Asn Ala Cys Cys Glu Ala Cys Ala
    210                 215                 220
Asn Leu Lys Gly Ala Phe Leu Val Ala Val Val Phe Leu Val Ile Cys
225                 230                 235                 240
Leu Ala Val Thr Leu Ile Phe Ala Lys Glu Val Pro Tyr Arg Gly Asn
                245                 250                 255
Glu Asn Leu Pro Thr Lys Ala Asn Gly Glu Val Glu Ala Glu Pro Thr
            260                 265                 270
Gly Pro Leu Ala Val Leu Lys Gly Phe Lys Asn Leu Pro Pro Gly Met
        275                 280                 285
Pro Ser Val Leu Leu Val Thr Gly Leu Thr Trp Leu Ser Trp Phe Pro
290                 295                 300
Phe Ile Leu Tyr Asp Thr Asp Trp Met Gly Arg Glu Ile Tyr His Gly
305                 310                 315                 320
Asp Pro Lys Gly Ser Asn Ala Gln Ile Ser Ala Phe Asn Glu Gly Val
                325                 330                 335
Arg Val Gly Ala Phe Gly Leu Leu Leu Asn Ser Ile Ile Leu Gly Phe
            340                 345                 350
Ser Ser Phe Leu Ile Glu Pro Met Cys Arg Lys Leu Gly Pro Arg Val
        355                 360                 365
Val Trp Val Thr Ser Asn Phe Met Val Cys Val Ala Met Ala Ala Thr
370                 375                 380
Ala Leu Ile Ser Tyr Trp Ser Leu Lys Asp Tyr His Gly Tyr Val Gln
385                 390                 395                 400
Asp Ala Ile Thr Ala Ser Thr Asn Ile Lys Ala Val Cys Leu Val Leu
                405                 410                 415
Phe Ala Phe Leu Gly Val Pro Leu Ala Ile Leu Tyr Ser Val Pro Phe
            420                 425                 430
Ala Val Thr Ala Gln Leu Ala Ala Thr Lys Gly Gly Gln Gly Leu
        435                 440                 445
Cys Thr Gly Val Leu Asn Ile Ser Ile Val Ile Pro Gln Val Ile Ile
    450                 455                 460
Ala Leu Gly Ala Gly Pro Trp Asp Ala Leu Phe Gly Lys Gly Asn Ile
465                 470                 475                 480
Pro Ala Phe Gly Val Ala Ser Gly Phe Ala Leu Ile Gly Gly Val Val
                485                 490                 495
Gly Val Phe Leu Leu Pro Lys Ile Ser Lys Arg Gln Phe Arg Ala Val
            500                 505                 510
Ser Ala Gly Gly His
        515

<210> SEQ ID NO 14
<211> LENGTH: 699
<212> TYPE: DNA
<213> ORGANISM: Anabaena cylindrica
<220> FEATURE:
<221> NAME/KEY: misc_feature
<223> OTHER INFORMATION: Anabaena cylindrica acyl-ACP reducatase (AR)
      coding sequence

<400> SEQUENCE: 14
atgcagcagc ttgttgagca aattgaaaaa attgatttcc aaagtgaaga atacaaagac        60
gcatatagcc gtattaatgc aattgtgatt gaaggggaac aagaagccca tgataattac       120
attcaactgg cggaactgct gccagaaagt aaagacaacc tgattcgctt atcgaagatg       180
gaaagccgtc acaagaaagg atttgaagct tgtggacgca atttgcaggt cacaccagac       240
```

| | |
|---|---|
| atgaagtttg caaaagagtt tttctcagga ctgcacaaaa attttcaaac tgcggccgca | 300 |
| gaaggtaaag ttgttacttg cttgctgatt caagctttaa ttatcgaatg ttttgcgatc | 360 |
| gcagcataca acatctacat tcccgtcgct gatgatttcg cccgcaaaat tacagaaggt | 420 |
| gtggtcaaaa agaatacag tcatctcaat tttggcgaag tttggcttca agaaaacttt | 480 |
| gcagaatcca aagctgaatt agaaacagct aaccgccaaa atcttcccct agtctggaag | 540 |
| atgctcaacc aagtagcaga tgatgcccac gtcttggcaa tggaaaaaga agccttagta | 600 |
| gaagatttca tgattcaata cggtgaggca ctaagtaata ttggcttcac aactcgtgat | 660 |
| attatgcgtc tctccgctta cggactcata cctgtctaa | 699 |

<210> SEQ ID NO 15
<211> LENGTH: 1020
<212> TYPE: DNA
<213> ORGANISM: Anabaena cylindrica
<220> FEATURE:
<221> NAME/KEY: misc_feature
<223> OTHER INFORMATION: Anabaena cylindrica aldehyde decarbonylase (AD) coding sequence

<400> SEQUENCE: 15

| | |
|---|---|
| atgtttggtc taattggaca tctgactagc ttagaacacg ctcaatccgt agctcaagaa | 60 |
| ttgggatacc cagaatatgc cgatcaaggg ctagactttt ggtgtagcgc cccgccgcaa | 120 |
| attgtcgatc acattaccgt taccagcatc accggacaaa aaattgaagg tcggtatgta | 180 |
| gaatcttgct ttttgccgga aatgctggca aatcgccgca ttaaagctgc aactcgcaaa | 240 |
| attctcaacg ccatggctca tgctcaaaag catggcattg atatcacggc tttaggtggg | 300 |
| ttttcttcaa ttattttga gaacttcaat ttagagcagt ttagccaagt ccgaaacgtt | 360 |
| aaattagaat ttgaacgctt cacaacagga atacccata cagcctacat catctgtcgg | 420 |
| caggtagagg aagcatctaa gcaattagga atagaattgt caaaagcaac tgtggctgtg | 480 |
| tgtggcgcta caggggatat tggcagtgca gttacccgct ggttagataa aaaaacagat | 540 |
| gtccaagaat tactcctcat agcccgtaac caagaacgtc ttcaagaact acaagcagaa | 600 |
| ttgggacggg gtaaaatcat gggtttacag gaagcattac cccaagccga tattgtagtt | 660 |
| tgggttgcta gtatgcctaa aggtgtagaa attgaccca cgtactgaa acaaccttgt | 720 |
| ttgctgattg atggtggcta tcctaaaaac ttagggacaa aaattcagca tcctggcgtg | 780 |
| tatgtattaa atggtggaat tgtcgagcat tccctagata ttgactggaa aattatgaaa | 840 |
| attgtcaata tggatgtccc agcacgccag ttgtttgctt gttttgcgga atcaatgctg | 900 |
| ctggaatttg agaagttata cacaaacttt tcttggggtc gtaatcagat taccgtagat | 960 |
| aaaatggagc aaattggtcg ggtgtcaatt aaacacggtt ttagaccatt attagtttag | 1020 |

<210> SEQ ID NO 16
<211> LENGTH: 1844
<212> TYPE: DNA
<213> ORGANISM: Pinus sabiniana
<220> FEATURE:
<221> NAME/KEY: misc_feature
<223> OTHER INFORMATION: MboS

<400> SEQUENCE: 16

| | |
|---|---|
| atggctctgc tctctgtcgc accgctggct cccagatggt gcgtgcacaa atcgttggtc | 60 |
| acttctacca aggttaaggt tgtccgcaga acgatctcaa cttccatccg catgtgtcgg | 120 |
| ataaccactg aatccggtga aggcgtacag agacgcatag caaatcatca ttccaacctc | 180 |

-continued

```
tgggacgata atttcataca gtccctctca acgccttatg gggcaatttc gtaccatgaa      240
agtgctcaga aacttattgg agaagtaaaa gagatgatca attcaatctc gcttaaagat      300
ggagaattaa tcaccccctc caatgatctc cttatgcggc tctctatagt cgatagcatt      360
gaacgtttgg gaatcgatag gcatttcaaa agtgaaataa aatcagctct ggattatgtt      420
tacagttatt ggaacgaaaa aggcattggg tggggaagag atagtgttgt tgccgatctc      480
aactcaactg ccttggggct tcgaactcta cgactacacg gatacccggt gtcttcagat      540
gtgttacaac acttcaaaga acaaaaaggg cagtttgcat gttcggccat tcaaacagag      600
ggagagataa gaagtgttct caacttattt cgggcttccc aaattgcctt tccgggagag      660
aaagttatgg aagaggcaga agtcttctct acaatatatt taaaagaagc catactaaag      720
cttccggtct gcggtctttc acgagagata tcgtacgttc tggaatatgg ttggcatata      780
aatttgccaa gattggaagc aaggaactac atcgacgtat ttggagagga ccccatttat      840
ttgacgccaa atatgaagac ccaaaaactt ctagaacttg caaagttgga gttcaatatg      900
tttcactctt tacaacagca agagctaaag cttctctcca gatggtggaa agattcgggt      960
ttctctcaaa tgaccttccc tcggcatcgt cacgtggaat attcactttt ggcatcttgc     1020
attgatagtg aacctcaaca ttcttcgttc agacttggat ttgccaaaat ctttcatctt     1080
gccacggttc ttgacgatat ttacgacacc tttggcacga tggatgagct agaactcttc     1140
acggcggcag ttaagaggtg gcatccgtct gcgacggagt ggcttccaga atatatgaaa     1200
ggagtatata tggtgcttta cgaaaccgtt aacgaaatgg caggagaagc agaaaagtct     1260
caaggccgag acacgctcaa ctatgccga aatgctttgg aggcttatat tgatgcttct     1320
atggaagaag cgaagtggat tttcagtggt tttttgccaa catttgagga gtacctggat     1380
aacgggaaag ttagtttcgg ttatggcatt ggcacattgc aacccattct gacgttgggc     1440 attcccttc ctcatcacat cctacaagaa atagactttc cttccaggct caatgatgtg     1500
gcatcttcca ttctccgact aaaaggcgac attcacactt accaggctga gaggagccgt     1560
ggagaaaaat cttcgtgtat atcatgttat atggaagaga atcccgagtc aacagaggaa     1620
gatgcaatca atcatatcaa ctccatggtc gacaaattac tcaaggaact aaattgggag     1680
tatctgagac ctgatagcaa tgttccaatc acttccaaga aacatgcatt tgacattctg     1740 agagcttct accatctcta caaataccga gatggcttca gcgttgcgaa ctatgaaata     1800
aagaatttgg tcatgacaac cgtcattgag cctgtgcctt tata                     1844
```